(12) United States Patent
Marion et al.

(10) Patent No.: US 8,415,348 B2
(45) Date of Patent: Apr. 9, 2013

(54) NITROGENATED DERIVATIVES OF PANCRATISTATIN

(75) Inventors: Frédéric Marion, Toulouse (FR); Jean-Philippe Annereau, Toulouse (FR); Jacques Fahy, Labruguiere (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 13/055,947

(22) PCT Filed: Jul. 28, 2009

(86) PCT No.: PCT/EP2009/059715
§ 371 (c)(1), (2), (4) Date: Jan. 26, 2011

(87) PCT Pub. No.: WO2010/012714
PCT Pub. Date: Feb. 4, 2010

(65) Prior Publication Data
US 2011/0123516 A1 May 26, 2011

(30) Foreign Application Priority Data
Jul. 28, 2008 (FR) ..................................... 08 55161

(51) Int. Cl.
- A61K 31/473 (2006.01)
- A61K 31/4525 (2006.01)
- C07D 491/06 (2006.01)
- C07D 405/14 (2006.01)
- C07D 413/04 (2006.01)
- A61P 35/00 (2006.01)

(52) U.S. Cl. ....... 514/232.8; 514/81; 514/280; 514/287; 544/148; 546/23; 546/48; 546/65

(58) Field of Classification Search ............................ None
See application file for complete search history.

(56) References Cited

U.S. PATENT DOCUMENTS

| | | | | |
|---|---|---|---|---|
| 4,866,071 A * | 9/1989 | Pettit | ............................. | 514/287 |
| 4,985,436 A * | 1/1991 | Pettit | ............................. | 514/287 |
| 5,529,989 A * | 6/1996 | Pettit et al. | ....................... | 514/81 |
| 7,541,346 B2 * | 6/2009 | Pettit et al. | ....................... | 514/89 |
| 7,709,643 B2 * | 5/2010 | Pettit et al. | ....................... | 546/23 |
| 7,994,320 B2 * | 8/2011 | Pettit et al. | ....................... | 546/23 |
| 2010/0076005 A1 * | 3/2010 | Ingrassia et al. | .............. | 514/280 |
| 2011/0306629 A1 * | 12/2011 | Hudlicky et al. | .............. | 514/287 |

OTHER PUBLICATIONS

Ceriotti, "Narciclasine: An Antiomitotic Substance from Narcissus Bulbs," Nature, 1967, pp. 595-596.
Chang et al., "A Practical Route to Enantiopure 1,2-Aminoalcohols," Tetrahedron Letters, 1996, vol. 37, No. 19, pp. 3219-3222.
Cree et al., "Measurement of Cytotoxicity by ATP-based Luminescence Assay in Primary Cell Cultures and Cell Lines," Toxicology in Vitro, 1997, vol. 11, pp. 553-556.
Gao et al., "Vicinal Diol Cyclic Sulfates: Like Epoxides Only More Reactive," J. Am. Chem. Soc., 1988, vol. 110, No. 22, pp. 7538-7539.
Geall et al., "Homologation of Polyamines in the Rapid Synthesis of Lipospermine Conjugates and Related Lipoplexes," Tetrahedron, 2000, vol. 56, pp. 2449-2460.
International Search Report in International Application No. PCT/EP2009/059715 mailed Oct. 10, 2009.
Lohray et al., "One Pot Synthesis of Homochiral Aziridines and Aminoalcohols from Homochiral 1,2-cyclic Sulfates," Tetrahedron Letters, 1989, vol. 30, No. 20, pp. 2623-2626.
Manpadi et al., "Total Syntheses of Pancreatistatin. A Review," Org. Prep. Proc. Int., 2008, vol. 40, pp. 109-161.
Padwa et al., "Synthesis of Some Members of the Hydroxylated Phenanthridone Sub-class of the Amaryllidaceae Alkaloid Family," J. Org. Chem., 2007, vol. 72, No. 7, pp. 2570-2582.
Pettit et al., "Antineoplastic Agents 450 Synthesis of (+)-Pancratistatin from (+)-Narciclasine as Relay," J. Org. Chem., 2001, vol. 66, pp. 2583-2587.
Pettit et al., "Isolation and Structure of Pancratistatin," J. Chem. Soc. Chem. Commun., 1984, vol. 24, pp. 1693-1694.

* cited by examiner

*Primary Examiner* — Fiona T Powers
(74) *Attorney, Agent, or Firm* — Birch, Stewart, Kolasch & Birch, LLP

(57) ABSTRACT

The present invention concerns nitrogenated derivatives of narciclasine and pancratistatin of the following general formula (I) as well their pharmaceutically acceptable salts. The present invention also concerns the use of these compounds in cancer therapy as well as a method for their preparation.

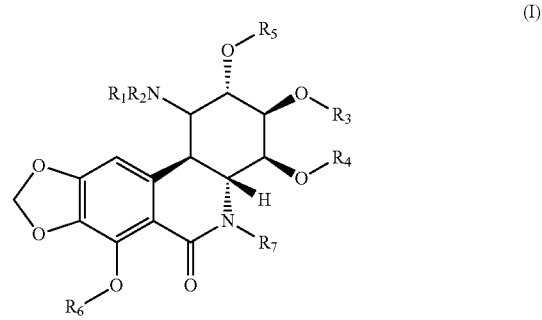

20 Claims, No Drawings

NITROGENATED DERIVATIVES OF PANCRATISTATIN

The present invention concerns nitrogenated derivatives of narciclasine and pancratistatin, as well as a method for their preparation and their use in cancer chemotherapy.

Narciclasine 1 is part of the alkaloids of the Amaryllidaceae family. Isolated from narcissus bulbs, its cytotoxic properties were described in 1967 [*Nature*, 213, 595-6, (1967)]. Later, pancratistatin 2, a close derivative of narciclasine, was isolated from *Pancratium littorale* [*J. Chem. Soc. Chem. Commun.*, 24, 1693-4, (1984)].

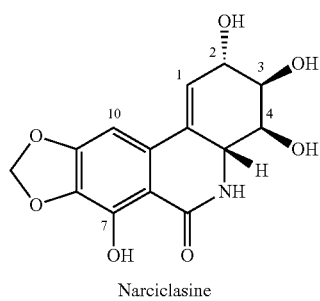

Narciclasine

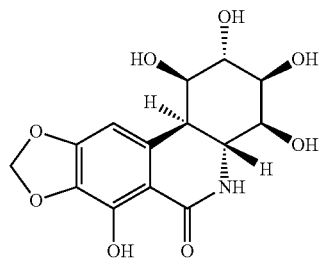

Pancratistatin

The cytotoxic activities of these compounds led to the development of research aiming to apply these properties to cancer treatment. Given the relatively low content observed in the plant and difficulties with extraction, several access paths based on the total synthesis of these derivatives have been developed [*Org. Prep. Proc. Int.*, 40, 109-61, (2008)], with the aim of preparing narciclasine and pancratistatin or corresponding prodrugs. Narciclasine, which is more abundant, was also described as an interesting precursor for obtaining pancratistatin [*J. Org. Chem.*, 66, 2583-7, (2001)].

However, in the field of medicinal chemistry, very few derivatives of narciclasine have been described to date. Furthermore, narciclasine and its derivatives often suffer from their low solubility in aqueous solvents or pharmaceutically acceptable mediums.

The inventors thus discovered that introducing a nitrogenated group in position 1 of the narciclasine made it possible to obtain derivatives with cytotoxic properties similar or superior (up to 10 times) to those of narciclasine and with better solubility in aqueous solvents in relation to narciclasine. Indeed, the presence of a salifiable nitrogenated group makes it possible to increase the solubility of the compounds of the invention without decreasing their cytotoxic activity.

The present invention thus concerns a compound with the following general formula (I):

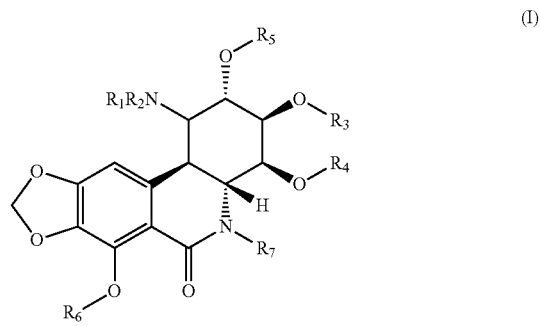

or a pharmaceutically acceptable salt thereof, an isomer or a mixture of isomers in all proportions, in particular a mixture of enantiomers, and in particular a racemate mixture, in which:

$R_1$ represents a hydrogen atom or a linear or branched $C_1$ to $C_6$ alkyl, linear or branched $C_2$ to $C_6$ alkenyl, linear or branched $C_2$ to $C_6$ alkynyl, aryl or arylalkyl group, $R_2$ represents a hydrogen atom, a saturated or unsaturated 3- to 7-membered hydrocarbon cycle, a 3- to 7-membered heterocycle or a linear or branched $C_1$ to $C_6$ alkyl, linear or branched $C_2$ to $C_6$ alkenyl, linear or branched $C_2$ to $C_6$ alkynyl, optionally substituted aryl, optionally substituted arylalkyl, C(O)R', $SO_2$—R', C(O)OR', C(O)NHR', NH=CNHR', C(=NR''')R', C(S)R', C(S)OR', C(S)NHR' group, where R' and R''' represent, independently of each other, a hydrogen atom, a saturated or unsaturated 3- to 7-membered hydrocarbon cycle, an optionally substituted 3- to 7-membered heterocycle, a linear or branched $C_1$ to $C_6$ alkyl, linear or branched $C_2$ to $C_6$ alkenyl, linear or branched $C_2$ to $C_6$ alkynyl, $C_1$ to $C_6$ hydroxyalkyl, $C_1$ to $C_6$ aminoalkyl, optionally substituted polyamine, polyether, optionally substituted aryl, optionally substituted arylalkyl or optionally substituted heteroaryl group, or $R_1$ and $R_2$ form together, with the nitrogen atom bearing them, an optionally substituted heteroaryl or a 3- to 7-membered heterocycle, which can comprise 1 to 3 additional heteroatoms, and optionally substituted by a linear or branched $C_1$ to $C_6$ alkyl, linear or branched $C_2$ to $C_6$ alkenyl, linear or branched $C_2$ to $C_6$ alkynyl, arylalkyl or heteroaryl group, $R_3$, $R_4$, $R_5$ and $R_6$ represent, independently of each other, a hydrogen atom, a saturated or unsaturated 3- to 7-membered hydrocarbon cycle or a $SO_3H$, $PO_3H_2$, C(O)OH, C(O)R'', C(O)OR'', C(O)NHR'', C(S)R'', C(S)OR'', C(S)NHR'' group, where R'' represents a hydrogen atom; a saturated or unsaturated 3- to 7-membered hydrocarbon cycle; a 3- to 7-membered heterocycle optionally substituted with a linear or branched $C_1$ to $C_6$ alkyl group; a linear or branched $C_1$ to $C_6$ alkyl; linear or branched $C_2$ to $C_6$ alkenyl; linear or branched $C_2$ to $C_6$ alkynyl; $C_1$ to $C_6$ hydroxyalkyl; $C_1$ to $C_6$ aminoalkyl; optionally substituted polyamine; polyether; optionally substituted aryl; or optionally substituted heteroaryl group, or $R_3$ and $R_4$ together form a —$CR_8R_9$—, —$SO_2$— or —$PO_2H$— chain binding the oxygen atoms bearing them, R7 represents a hydrogen atom, a linear or branched $C_1$ to $C_6$ alkyl, linear or branched $C_2$ to $C_6$ alkenyl or linear or branched $C_2$ to $C_6$ alkynyl group or a saturated or unsaturated 3- to 7-membered hydrocarbon cycle, and R$_8$ and R$_9$ represent, independently of each other, a hydrogen atom or a linear or branched C$_1$ to C$_6$ alkyl group, such as a methyl.

In the present invention, "pharmaceutically acceptable" refers to that which is useful in the preparation of a pharmaceutical composition which is generally safe, nontoxic and neither biologically nor otherwise undesirable, and which is acceptable for veterinary use as well as human pharmaceutical use.

"Pharmaceutically acceptable salts" of a compound designates, in the present invention, salts which are pharmaceutically acceptable, as defined above, and which posses the desired pharmacological activity of the parent compound.

This involves in particular acid addition salts formed with inorganic acids such as hydrochloric acid, hydrobromic acid, sulfuric acid, nitric acid, phosphoric acid and similar; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and similar.

In the present invention, "isomers" designates diastereoisomers or enantiomers. These are therefore optical isomers also called "stereoisomers". Stereoisomers which are not mirror images of each other are thus designated by the term "diastereoisomers", and stereoisomers which are non-superimposable mirror images of each other are designated by the term "enantiomers".

A carbon atom bound to four non-identical radicals is called a "chiral center".

An equimolar mixture of two enantiomers is called a racemate mixture.

In the sense of the present invention, "halogen" refers to a fluorine, chlorine, bromine or iodine atom.

"Linear or branched C$_1$ to C$_6$ alkyl" or "(C$_1$-C$_6$)alkyl" designates, in the sense of the present invention, a linear or branched saturated hydrocarbon chain comprising 1 to 6 carbon atoms. This may be in particular a methyl, ethyl, n-propyl, isopropyl, n-butyl, iso-butyl, sec-butyl, tert-butyl, n-pentyl or n-hexyl group.

"Linear or branched C$_1$ to C$_6$ haloalkyl" designates, in the sense of the present invention, a linear or branched C$_1$ to C$_6$ alkyl group as defined above, substituted by one or several halogen atoms, in particular by one or several fluorine or chlorine atoms. This may be in particular a —CF$_3$ or —CH$_2$Cl group.

"Linear or branched C$_2$ to C$_6$ alkenyl" or "(C$_2$-C$_6$)alkenyl" designates, in the sense of the present invention, a linear or branched hydrocarbon chain comprising 2 to 6 carbon atoms and comprising at least one double bond. This may be in particular a vinyl or allyl group.

"Linear or branched C$_2$ to C$_6$ alkynyl" designates, in the sense of the present invention, a linear or branched hydrocarbon chain comprising 2 to 6 carbon atoms and comprising at least one triple bond. This may be in particular an ethynyl or propynyl group.

"C$_1$ to C$_6$ hydroxyalkyl" designates, in the sense of the present invention, an OH group bound to the molecule via a linear or branched C$_1$ to C$_6$ alkyl group, preferably linear, as defined above. It may be in particular a —(CH$_2$)$_n$OH group where n represents an integer comprised between 1 and 6.

"C$_1$ to C$_6$ aminoalkyl" designates, in the sense of the present invention, an NH$_2$ group bound to the molecule via a linear or branched C$_1$ to C$_6$ alkyl group, preferably linear, as defined above. It may be in particular a —(CH$_2$)$_n$NH$_2$ group where n represents an integer comprised between 1 and 6.

"Polyether" designates, in the sense of the present invention, a linear hydrocarbon chain comprising 6 to 25 carbon atoms, at least two of these carbon atoms being replaced with oxygen atoms, with the condition that two oxygen atoms can not be located in adjacent positions. This may be in particular a PEG (poly(ethylene glycol)) chain comprising notably 2 to 7 ethylene glycol monomers.

"Polyamine" designates, in the sense of the present invention, a linear hydrocarbon chain comprising 6 to 15 carbon atoms, at least two of these carbon atoms being replaced with nitrogen atoms, with the condition that two nitrogen atoms can not be located in adjacent positions. Said polyamine may in particular meet the following formula:

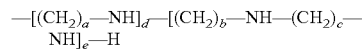

with a, b and c representing, independently of each other, an integer comprised between 1 and 5 and d and e each representing 0 or 1.

As an example, it may be a spermidine-type chain, i.e. with formula —(CH$_2$)$_4$—NH—(CH$_2$)$_3$—NH$_2$ or —(CH$_2$)$_3$—NH—(CH$_2$)$_4$—NH$_2$, a spermine-type chain with formula —(CH$_2$)$_3$—NH—(CH$_2$)$_4$—NH—(CH$_2$)$_3$—NH$_2$ or a chain with formula —(CH$_2$)$_4$—NH—(CH$_2$)$_4$—NH—(CH$_2$)$_4$—NH$_2$.

This polyamine may optionally be substituted, more particularly on the nitrogen atoms, in particular by an N-protector group such as (C$_1$-C$_6$)alkyl, (C$_2$-C$_6$)alkenyl, —CO—(C$_1$-C$_6$)alkyl, —CO—(C$_2$-C$_6$)alkenyl, —CO$_2$—(C$_1$-C$_6$)alkyl or —CO$_2$—(C$_2$-C$_6$)alkenyl.

Said optionally substituted polyamine may then meet the following general formula:

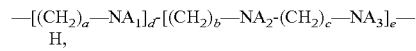

a, b, c, d and e being as defined above and A$_1$, A$_2$ and A$_3$, different or preferably identical, representing a hydrogen atom or an N-protector group such as (C$_1$-C$_6$)alkyl, (C$_2$-C$_6$) alkenyl, —CO—(C$_1$-C$_6$)alkyl, —CO—(C$_2$-C$_6$)alkenyl, —CO$_2$—(C$_1$-C$_6$)alkyl or —CO$_2$—(C$_2$-C$_6$)alkenyl.

"Protector group" designates, in the sense of the present invention, a group which selectively blocks a reactive site in a multifunctional compound such that a chemical reaction may be carried out selectively at another unprotected reactive site in the meaning traditionally associated with this in synthesis chemistry.

"N-protector group" designates, in the sense of the present invention, any substituent which protects the NH or NH$_2$ group against undesirable reactions such as the N-protector groups described in Greene, "Protective Groups In Organic synthesis", (John Wiley & Sons, New York (1981)) et Harrison et al. "Compendium of Synthetic Organic Methods", Vols. 1 to 8 (J. Wiley & sons, 1971 to 1996). The N-protector groups comprise carbamates (such as —CO$_2$—(C$_1$-C$_6$)alkyl or —CO$_2$—(C$_2$-C$_6$)alkenyl), amides (such as —CO—(C$_1$-C$_6$)alkyl, —CO—(C$_2$-C$_6$)alkenyl), N-alkyl or N-alkenyl derivatives, amino acetal derivatives, N-benzyl derivatives, imine derivatives, enamine derivatives and N-heteroatom derivatives. In particular, the N-protector group includes formyl, acetyl, benzoyl, pivaloyl, phenylsulfonyl, benzyl (Bn), t-butyloxycarbonyl (Boc), benzyloxycarbonyl (Cbz), p-methoxybenzyloxycarbonyl, p-nitrobenzyl-oxycarbonyl, trichloroethoxycarbonyl (TROC), allyloxycarbonyl (Alloc), 9-fluorenylmethyloxycarbonyl (Fmoc), trifluoroacetyl, benzyl carbamates (substituted or not) and similar. It may be in particular a Boc group.

"Aryl" designates, in the sense of the present invention, an aromatic group, preferably comprising 5 to 10 carbon atoms and comprising one or several fused cycles, such as a phenyl or naphthyl group, for example. Advantageously, it is phenyl.

This aryl group may optionally be substituted, in particular by one or several groups chosen among a halogen atom, an optionally substituted polyamine, a linear or branched $C_1$ to $C_6$ alkyl, linear or branched $C_1$ to $C_6$ haloalkyl, —CN, —$NO_2$, —$OA_4$, —$SO_2A_4$, —$NA_5A_6$ and -(linear or branched $C_1$ to $C_6$ alkyl)-$NA_5A_6$ (in particular —$CH_2$—$NA_5A_6$) group with:

$A_4$ representing a hydrogen atom or a linear or branched $C_1$ to $C_6$ alkyl group, and $A_5$ and $A_6$ representing, independently of each other, a hydrogen atom, a linear or branched $C_1$ to $C_6$ alkyl group or a saturated or unsaturated 3- to 7-membered hydrocarbon cycle, or $A_5$ and $A_6$ together forming, with the nitrogen atom bearing them, a 3- to 7-membered heterocycle, saturated or unsaturated, which can comprise 1 to 3 additional heteroatoms, and optionally substituted with a linear or branched $C_1$ to $C_6$ alkyl group.

"Heteroaryl" group designates, in the sense of the present invention, any aryl group as defined above in which one or several carbon atoms have been replaced by one or several heteroatoms, advantageously 1 to 4, such as sulfur, nitrogen or oxygen atoms, for example. Examples of heteroaryl groups are furyl, thiophenyl, pyrrolyl, pyridyl, pyrimidyl, pyrazolyl, imidazolyl, triazolyl, tetrazolyl or indyl groups.

This heteroaryl group may optionally be substituted, in particular by one or several groups chosen among a halogen atom and a linear or branched $C_1$ to $C_6$ alkyl, —$OA_7$, —$NA_7A_8$ and —$SO_2A_7$ group with $A_7$ and $A_8$ designating a hydrogen atom or a linear or branched $C_1$ to $C_6$ alkyl group as previously defined.

"Arylalkyl group" designates, in the sense of the present invention, an aryl group as defined above bound to the molecule via a linear or branched $C_1$ to $C_6$ alkyl group as defined above. Preferably, it is a benzyl group.

This arylalkyl group may optionally be substituted, preferably on the aryl core, in particular by one or several groups chosen among a halogen atom, an optionally substituted polyamine, a linear or branched $C_1$ to $C_6$ alkyl, linear or branched $C_1$ to $C_6$ haloalkyl, —CN, —$NO_2$, —$OA_4$, —$SO_2A_4$, —$NA_5A_6$ and -(linear or branched $C_1$ to $C_6$ alkyl)-$NA_5A_6$ (in particular —$CH_2$—$NA_5A_6$) group with:

$A_4$ representing a hydrogen atom or a linear or branched $C_1$ to $C_6$ alkyl group, and $A_5$ and $A_6$ representing, independently of each other, a hydrogen atom, a linear or branched $C_1$ to $C_6$ alkyl group or a saturated or unsaturated 3- to 7-membered hydrocarbon cycle, or $A_5$ and $A_6$ together forming, with the nitrogen atom bearing them, a 3- to 7-membered heterocycle, saturated or unsaturated, which can comprise 1 to 3 additional heteroatoms, and optionally substituted with a linear or branched $C_1$ to $C_6$ alkyl group.

"Saturated or unsaturated" designates, in the sense of the present invention, that the group is saturated or comprises one or several unsaturations.

"Unsaturation" designates, in the present invention, a triple bond or a double bond, and preferably a double bond as it is present in a cycle.

"Saturated or unsaturated 3- to 7-membered hydrocarbon cycle", designates, in the sense of the present invention, a 3- to 7-membered hydrocarbon cycle which is saturated or comprises one or several double bonds. This may be in particular a cyclopropyl, cyclopentyl, cyclohexyl, cycloheptyl or cyclohexenyl group. Preferably, it is a saturated cycle or a cycle comprising one or several double bonds, preferably 1 or 2. Advantageously, the cycle will comprise 5 or 6 members.

"3- to 7-membered heterocycle" designates a hydrocarbon cycle, saturated or unsaturated, as defined above in which one or several carbon atoms have been replaced by one or several heteroatoms, advantageously 1 to 4 such as, for example, sulfur, nitrogen or oxygen atoms and preferably nitrogen atoms. This may be in particular a morpholinyl, piperazinyl, piperidinyl, pyrrolidinyl or triazolyl group.

"Heteroatoms" designates in particular a sulfur, nitrogen or oxygen atom.

According to one particular embodiment of the invention, $R_2$ represents a hydrogen atom, a saturated or unsaturated 3- to 7-membered hydrocarbon cycle, a 3- to 7-membered heterocycle or a linear or branched $C_1$ to $C_6$ alkyl, linear or branched $C_2$ to $C_6$ alkenyl, linear or branched $C_2$ to $C_6$ alkynyl, optionally substituted aryl, optionally substituted arylalkyl, C(O)R', $SO_2$—R', C(O)OR', C(O)NHR', NH=CNHR', C(S)R', C(S)OR', or C(S)NHR' group, where R' represents a 3- to 7-membered heterocycle, or a linear or branched $C_1$ to $C_6$ alkyl, linear or branched $C_2$ to $C_6$ alkenyl, linear or branched $C_2$ to $C_6$ alkynyl, $C_1$ to $C_6$ hydroxyalkyl, $C_1$ to $C_6$ aminoalkyl, polyamine, polyether, optionally substituted aryl, optionally substituted arylalkyl or optionally substituted heteroaryl group; or $R_1$ and $R_2$ form together, with the nitrogen atom bearing them, a heteroaryl or a 3- to 7-membered heterocycle, which can comprise 1 to 3 additional heteroatoms, and optionally substituted by a linear or branched $C_1$ to $C_6$ alkyl, linear or branched $C_2$ to $C_6$ alkenyl, linear or branched $C_2$ to $C_6$ alkynyl, arylalkyl or heteroaryl group.

In particular, the compounds of the invention meet the following formula (Ibis):

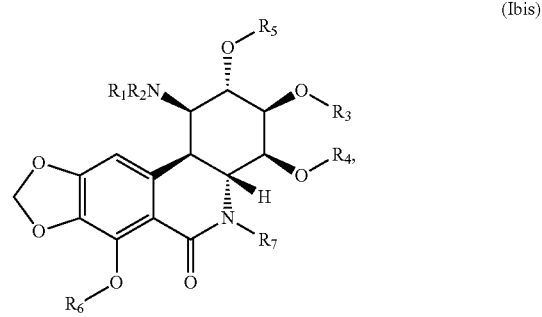

(Ibis)

for which $R_1$, $R_2$, $R_3$, $R_4$, $R_5$, $R_6$ and $R_7$ are as defined above.

According to a first specific embodiment, $R_2$ represents a hydrogen atom, a linear or branched $C_1$ to $C_6$ alkyl, linear or branched $C_2$ to $C_6$ alkenyl, linear or branched $C_2$ to $C_6$ alkynyl, aryl, arylalkyl C(O)R', $SO_2$—R', C(O)OR', or C(O)NHR' group, where R' represents a 3- to 7-membered heterocycle or a linear or branched $C_1$ to $C_6$ alkyl, linear or branched $C_2$ to $C_6$ alkenyl, linear or branched $C_2$ to $C_6$ alkynyl, $C_1$ to $C_6$ hydroxyalkyl, $C_1$ to $C_6$ aminoalkyl, polyamine, polyether, optionally substituted aryl, optionally substituted arylalkyl or optionally substituted heteroaryl group, and preferably where R' represents a linear or branched $C_1$ to $C_6$ linear alkyl group or an aryl, arylalkyl or heteroaryl group, the aryl core of said group being optionally substituted with one or several fluorine atoms, and $R_1$ is as defined above and advantageously represents a hydrogen atom or a linear or branched $C_1$ to $C_6$ alkyl group, and preferably represents a hydrogen atom.

According to a second specific embodiment, $R_1$ and $R_2$ form together, with the nitrogen atom bearing them, a heterocycle optionally comprising 1 or 2 nitrogen atoms, and preferably comprising 5 to 6 members, such as a piperidine or a 1,2,3-triazole, optionally substituted with a linear or branched $C_1$ to $C_6$ alkyl, linear or branched $C_2$ to $C_6$ alkenyl, linear or branched $C_2$ to $C_6$ alkynyl, aryl, arylalkyl or heteroaryl group.

Advantageously, $R_3$, $R_4$, $R_5$ and $R_6$ represent, independently of each other, a hydrogen atom or an $SO_3H$, $PO_3H_2$ or $C(O)OH$ group.

Even more advantageously, $R_3$, $R_5$ and $R_6$ each represent a hydrogen atom and $R_4$ represents a hydrogen atom or an $SO_3H$, $PO_3H_2$ or $C(O)OH$ group.

Equally advantageously, $R_3$ and $R_4$ each represent a hydrogen atom or together form a —$CR_8R_9$— chain as defined above, $R_5$ and $R_6$ advantageously each representing a hydrogen atom.

Preferably, all of the radicals $R_3$, $R_4$, $R_5$ and $R_6$ represent a hydrogen atom.

Advantageous, $R_7$ represents a hydrogen atom.

Preferably, the radicals $R_3$, $R_4$, $R_5$, $R_6$ and $R_7$ each represent a hydrogen atom.

According to one particular embodiment of the invention:
- $R_1$ represents a hydrogen atom or a linear or branched $C_1$ to $C_6$ alkyl group,
- $R_2$ represents a hydrogen atom, a saturated or unsaturated 3- to 7-membered hydrocarbon cycle, a linear or branched $C_1$ to $C_6$ alkyl, arylalkyl, —$C(O)R'$, —$SO_2R'$, —$C(O)OR'$, —$C(O)NHR'$ group,
- with $R'$ representing a saturated or unsaturated 3- to 7-membered hydrocarbon cycle, an optionally substituted 3- to 7-membered heterocycle, a linear or branched $C_1$ to $C_6$ alkyl, optionally substituted aryl, arylalkyl or heteroaryl group, or
- $R_1$ and $R_2$ form together, with the nitrogen atom bearing them, an optionally substituted heteroaryl or a 3- to 7-membered heterocycle, which can comprise 1 to 3 additional heteroatoms, and optionally substituted with an aryl group, and
- $R_3$, $R_4$, $R_5$, $R_6$ and $R_7$ each represent a hydrogen atom, or $R_3$ and $R_4$ together form a —$CR_8R_9$— chain,
- with $R_8$ and $R_9$ representing, independently of each other, a linear or branched $C_1$ to $C_6$ alkyl group, such as a methyl group.

According to another particular embodiment of the invention, the compounds of the invention meet the following formula (Ia) or (Ib):

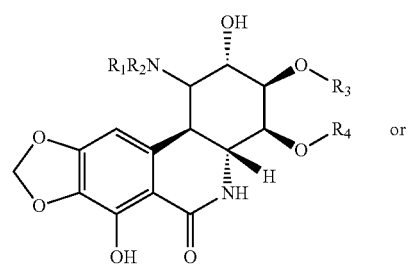

(Ia)

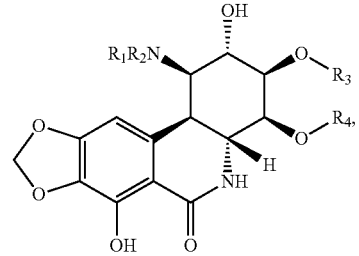

(Ib)

with $R_1$, $R_2$, $R_3$ and $R_4$ as defined above, and in particular with $R_3$ and $R_4$ each representing a hydrogen atom or possibly together forming a chain —$CR_8R_9$— as defined above.

Advantageously, $R_2$ represents a —$C(O)R'$ group with $R'$ representing an aryl group, preferably phenyl, optionally substituted, and $R_1$ is as defined above and advantageously represents a hydrogen atom.

In particular, the compounds of the invention may be chosen among the following compounds:

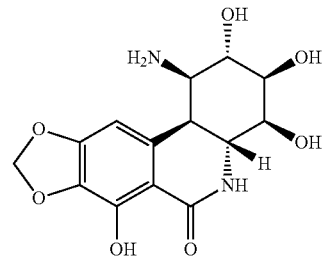

6

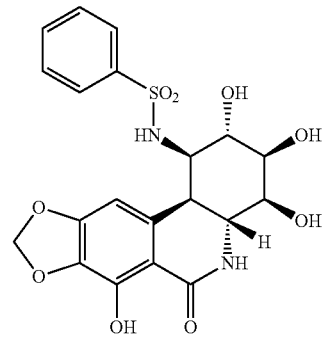

8

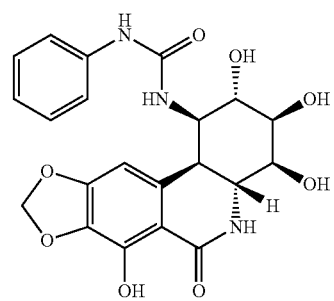

9

-continued
9
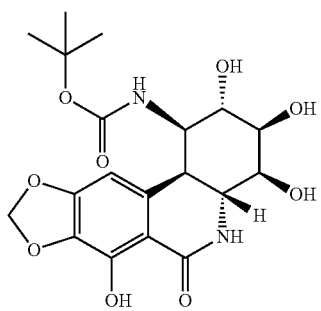
10
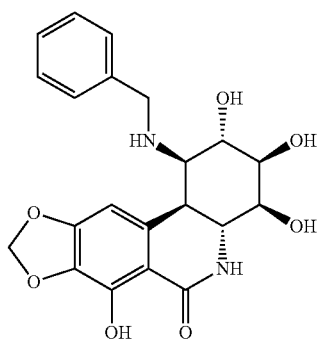
11
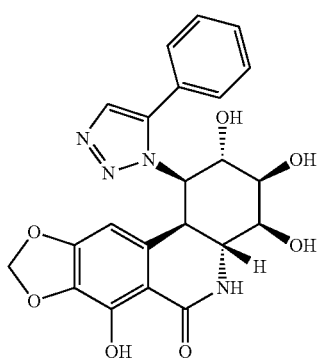
15
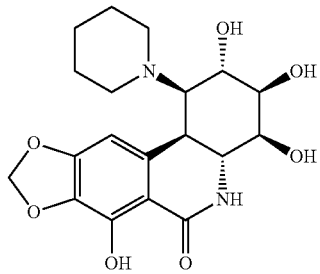
16
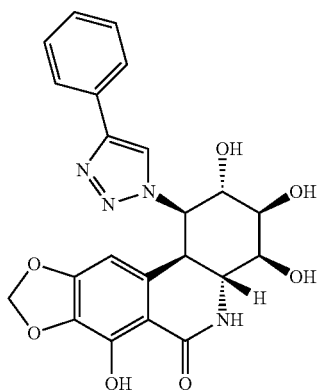
12
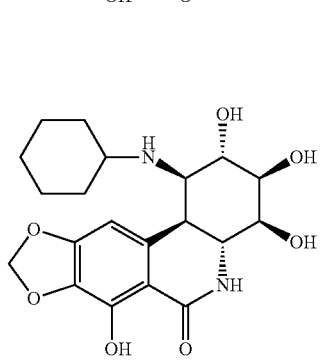
17
13
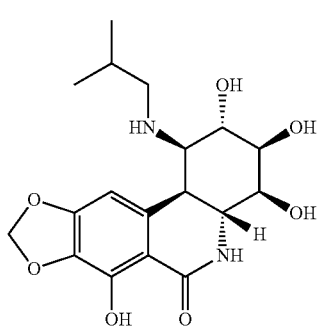
18
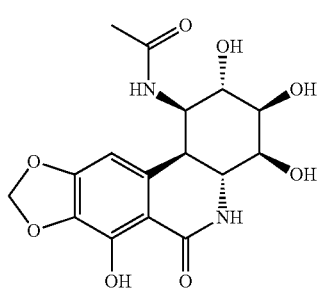

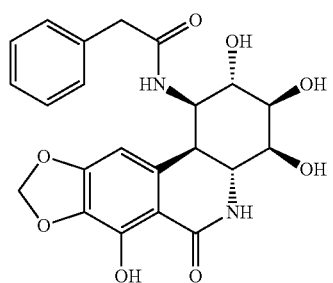
19
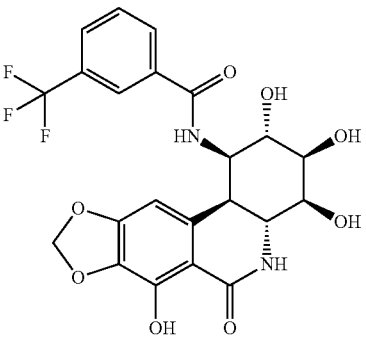
20
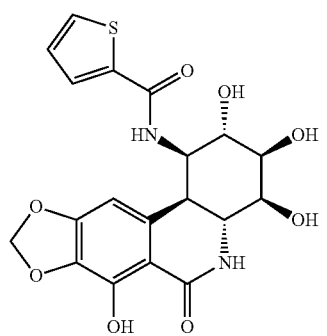
21
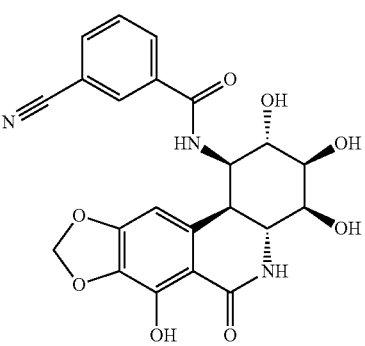
22
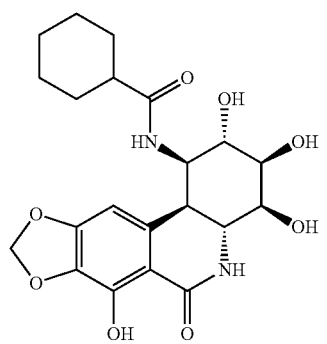
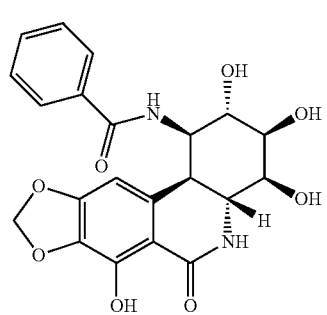
23
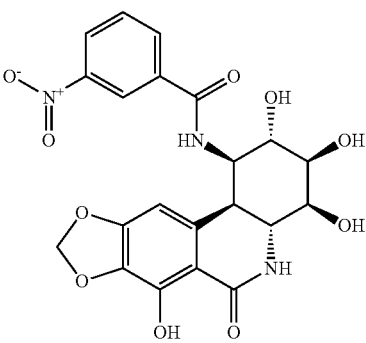
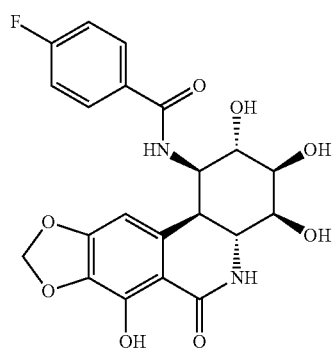
24
25
26
27
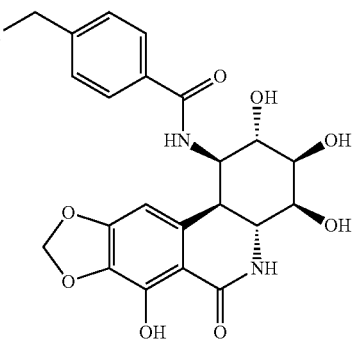

28
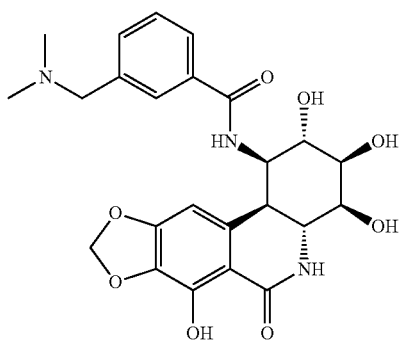
29
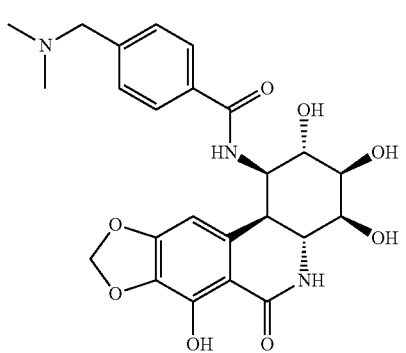
30
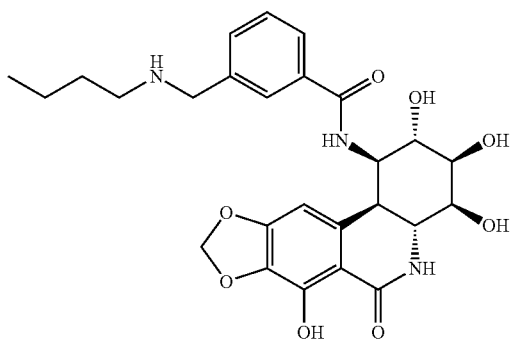
31
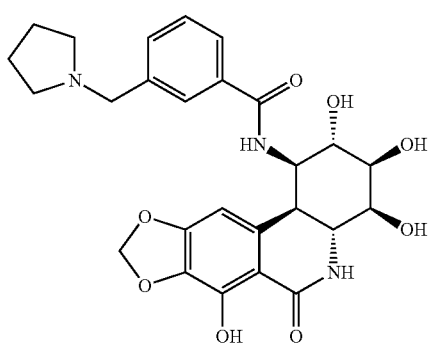
32
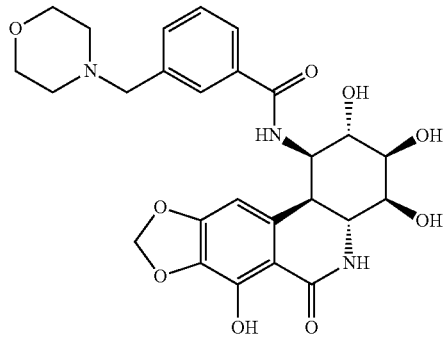
33
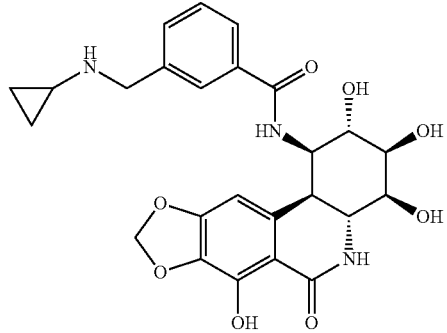
34
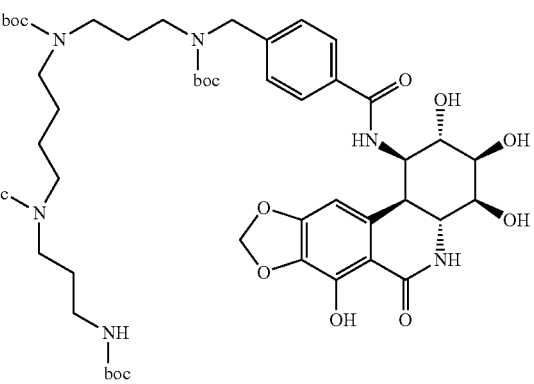
35
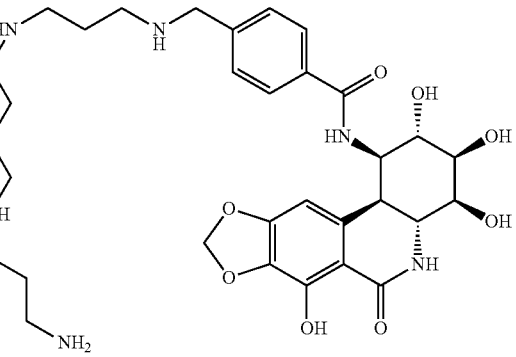

-continued

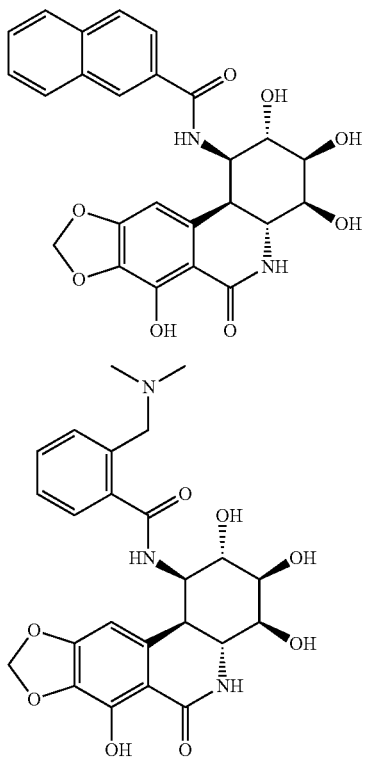

The present invention also concerns a compound of the invention as defined above for its use as a medicinal drug, in particular intended for cancer treatment.

The invention also concerns the use of a compound of the invention as defined above for the preparation of a medicinal drug, in particular intended for cancer treatment.

The invention also concerns a method for cancer treatment, including the administration of an effective quantity of at least one compound of the invention as defined above to a patient in need thereof.

The present invention also concerns a pharmaceutical composition comprising at least one compound according to the invention and at least one pharmaceutically acceptable excipient.

The compounds according to the invention can be administered by oral, sublingual, parenteral, subcutaneous, intramuscular, intravenous, transderm, local or rectal route, and preferably intravenously or orally.

In the pharmaceutical compositions of the present invention for oral, sublingual, parenteral, subcutaneous, intramuscular, intravenous, transderm, local or rectal administration, the active ingredient can be administered in unitary administration forms, mixed with traditional pharmaceutical mediums, to animals or humans. Suitable unitary administration forms include oral forms such as tablets, capsules, powders, granules and oral solutions or suspensions, sublingual and buccal forms of administration, parenteral, subcutaneous, intramuscular, intravenous, intranasal or intraocular forms of administration and rectal forms of administration.

When one prepares a solid composition in tablet form, one mixes the main active ingredient with a pharmaceutical excipient such as gelatin, starch, lactose, magnesium stearate, talc, gum Arabic, or similar. One can coat the tablets with sucrose or other suitable materials, or they can be processed such that they have an extended or delayed activity and continuously release a predetermined quantity of active principle.

One obtains a preparation in capsules by mixing the active ingredient with a diluent and pouring the mixture obtained in the soft or hard capsules.

A preparation in syrup or elixir form can contain the active ingredient jointly with a sweetener, an antiseptic, as well as an agent providing a suitable taste and coloring.

Powders or granules dispersible in water can contain the active ingredient mixed with dispersion agents or wetting agents, or suspension agents, like with taste correctors or sweeteners.

For rectal administration, one uses suppositories, which are prepared with binders which melt at rectal temperature, for example cocoa butter or polyethylene glycols.

For parenteral, intranasal or intraocular administration, one uses aqueous suspensions, isotonic saline solutions or sterile and injectable solutions which contain pharmacologically compatible dispersion agents and/or wetting agents.

The active principle can also be formulated in the form of microcapsules, possibly with one or several additive carriers.

The compounds of the invention can be used at doses between 0.01 mg and 1000 mg per day, given in a single dose once daily or administered in several doses throughout the day, for example twice daily in equal doses. The dose administered per day is advantageously between 5 mg and 500 mg, and more advantageously between 10 mg and 200 mg. It may be necessary to use doses outside these ranges, which one skilled in the art may realize himself.

In one particular embodiment, this composition may also include at least one other active principle, advantageously chosen among anti-cancer agents.

Anti-cancer agents may non-limitingly include 6-mercaptopurine, fludarabine, cladribine, pentostatin, cytarabine, 5-fluorouracile, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocin, carboplatin, cisplatin, oxaliplatin, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrozole, letrozole, tamoxifen, octreotide and lanreotide.

The present invention also concerns a pharmaceutical composition comprising:
(i) at least one compound of formula (I) as defined above, and
(ii) at least one other active principle, in particular useful for cancer treatment,
as combination products for simultaneous use, separate use or use spread over time.

By way of active principle, we can cite in particular and non-limitingly, 6-mercaptopurine, fludarabine, cladribine, pentostatin, cytarabine, 5-fluorouracile, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocin, carboplatin, cisplatin, oxaliplatin, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrozole, letrozole, tamoxifen, octreotide or lanreotide.

The pharmaceutical composition as described above can be useful in particular for cancer treatment.

The present invention also concerns the use of a pharmaceutical composition comprising:

(i) at least one compound of formula (I) as defined above, and (ii) at least one other active principle, in particular useful for cancer treatment, as combination products for simultaneous use, separate use or use spread over time, for the preparation of a medicinal drug intended for cancer treatment.

The present invention also concerns a method for preparing a compound according to the invention, characterized in that the compound of formula (I) is obtained by reaction of the following compound of formula (II):

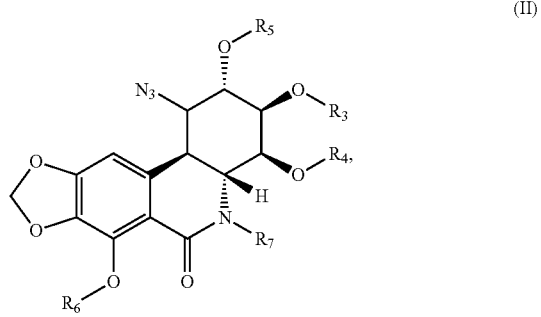

for which $R_3$, $R_4$, $R_5$, $R_6$ and $R_7$ are as defined above.

According to a first particular embodiment, the method for preparing a compound of formula (I) comprises the following successive steps:

(i) hydrogenolysis of the azide of the compound of formula (II) as defined above in free amine to yield a compound of formula (I) for which $R_1=R_2=H$, (ii) optionally one or several substitution steps of the free amine obtained in the preceding step (i) to yield a compound of formula (I) for which at least one of the groups $R_1$ and $R_2$ does not represent a hydrogen atom, and (iii) separation from the reaction medium of the compound of formula (I) obtained in the preceding step (i) or (ii).

This method may be followed by optional additional substitution and/or protection/deprotection reactions well known by those skilled in the art.

The hydrogenolysis is carried out under a hydrogen atmosphere, preferably in the presence of palladium on carbon. The reaction solvent may be tetrahydrofuran (THF), ethanol or a mixture of the two. Preferably, it will be an equimolar THF/ethanol mixture. Moreover, this step will advantageously be carried out at ambient temperature.

The substitution steps of the free amine, well known by those skilled in the art, may be in particular:

a reductive amination to provide access to secondary and tertiary amines, a reaction with an acyl chloride or an acid anhydride to give access to an amide, or to a thioamide after treatment notably with Lawesson's reagent (when $R_2=C(O)R'$ or $C(S)R'$), a reaction with a sulfonyl chloride to give access to the sulfonamides (when $R_2=SO_2-R'$), a reaction with a chloroformate or thionochloroformate or with a pyrocarbonate (such as tert-butyl pyrocarbonate) to give access to a carbamate or a thiocarbamate (when $R_2=C(O)OR'$ or $C(S)OR'$), a reaction with an isocyanate or isothiocyanate to give access to ureas or thioureas (when $R_2=C(O)NHR'$ or $C(S)NHR'$), a reaction with a nitrile in acid medium (Pinner reaction) when $R_2=C(=NR''')R'$ with $R'''=H$, or a reaction with an imidate when $R_2=C(=NR''')R'$) in particular with $R'''\neq H$, or a reaction with a 2-alkyl-2-thiopseudourea to give access to guanidines (when $R_2=NH=CNHR'$).

The separation step from the reaction medium may be carried out using methods well known by those skilled in the art, for example by extraction, evaporation of the solvent or precipitation and filtration.

The compound thus obtained may then be purified if necessary using techniques well known by those skilled in the art, such as by recrystallization if the compound is crystalline, by distillation, by silica gel column chromatography or by high performance liquid chromatography (HPLC).

According to a second particular embodiment, in the case of a compound of formula (I), for which $R_1$ and $R_2$ together form, with the nitrogen atom bearing them, a 1,2,3-triazole optionally substituted by a linear or branched $C_1$ to $C_6$ alkyl, linear or branched $C_2$ to $C_6$ alkenyl, linear or branched $C_2$ to $C_6$ alkynyl, aryl, arylalkyl or heteroaryl group, the method for preparing this compound of formula (I) includes the following successive steps:

(i) cycloaddition of the azide of the compound of formula (II) as defined above with an alkyne of formula A-C≡CH, for which A represents a hydrogen atom or a linear or branched $C_1$ to $C_6$ alkyl, linear or branched $C_2$ to $C_6$ alkenyl, linear or branched $C_2$ to $C_6$ alkynyl, aryl or heteroaryl group, and (ii) separation from the reaction medium of the compound of formula (I) obtained in the preceding step (i).

The cycloaddition reaction will advantageously be carried out in methanol, preferably hot, in particular at approximately 100° C.

The separation from the reaction medium of the compound of formula (I) thus obtained may be carried out using techniques well known by those skilled in the art, as indicated above. Likewise, a step of purification of the obtained product may be necessary and may be carried out using techniques known by those skilled in the art, some examples of which are cited above.

The compound of formula (II), for which the $N_3$ group is located on the same side of the cycle as the $OR_3$ group, can be obtained by nucleophile substitution with a mineral azide of the compound of the following formula (III):

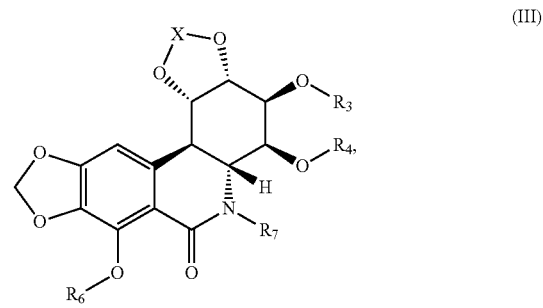

for which $R_3$, $R_4$, $R_6$ and $R_7$ are as previously defined and X represents a —SO—, —$SO_2$— or —CO— group, and preferably a —$SO_2$— group.

This compound of formula (II), for which the $N_3$ group is located on the same side of the cycle as the $OR_3$ group, thus makes it possible to access compounds of formula (Ibis).

"Mineral azide" designates in particular sodium, potassium, lithium or zinc azide. Preferably, it is sodium azide.

The reactivity of the sulfate, sulfite or cyclic carbonate groups to introduce a nitrogenated nucleophile radical by selective attack on position 1 is described in the following articles: *J. Am. Chem. Soc.*, 110, 17538-9, (1988); *Tetrahedron Lett.*, 30, 2623-6, (1989); *Tetrahedron Lett.*, 37, 3219-22, (1996). The teaching of these articles was applied to the following compounds 3 and 4.

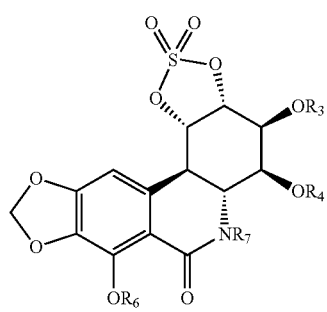

3

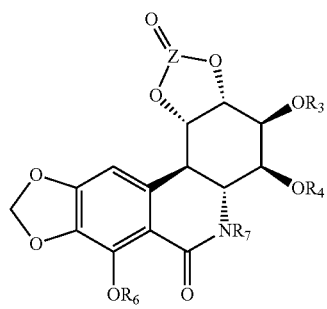

4

Z = C, S

Thus, advantageously, the nucleophile substitution is carried out in dimethylformamide, preferably hot, at a temperature of approximately 80° C.

Additional substitution, protection and/or deprotection reactions of the hydroxyl and amino groups, well known by those skilled in the art, may be necessary.

In particular, it may be advantageous to protect the oxygen atoms bearing the radicals $R_3$ and $R_4$ in the form of a cyclic acetal, i.e. these two oxygens are bound by a chain of formula —$CR_8R_9$— as previously defined, such as a chain —$CMe_2$-. This protection can be obtained by reaction of the corresponding free hydroxyl groups with the ketone of formula $R_8$—CO—$R_9$.

Once the nucleophile substitution is carried out with the azide, the cyclic acetal may be deprotected by acid hydrolysis, in particular in the presence of sulfuric acid.

Additional substitution, protection and/or deprotection reactions of the hydroxyl and amino groups, well known by those skilled in the art, may also be necessary, in particular as described above.

In the case of a compound of formula (II), for which the $N_3$ group is located on the same side of the cycle as the $OR_5$ group, one may consider introducing a halogen atom in position C-1 by nucleophile substitution from a compound of formula (III) as defined above. A second step of nucleophile substitution with a mineral azide of the halogenated derivative thus obtained would make it possible to obtain the desired compound of formula (II).

The compounds of formula (III) can be prepared according to the protocol described in the following articles: *J. Am. Chem. Soc.*, 117, 10143-4, (1995); *J. Org. Chem.*, 66, 2583-7, (2001); *J. Org. Chem.*, 72, 2570-82, (2007).

The present invention also concerns a compound with the following general formula (II):

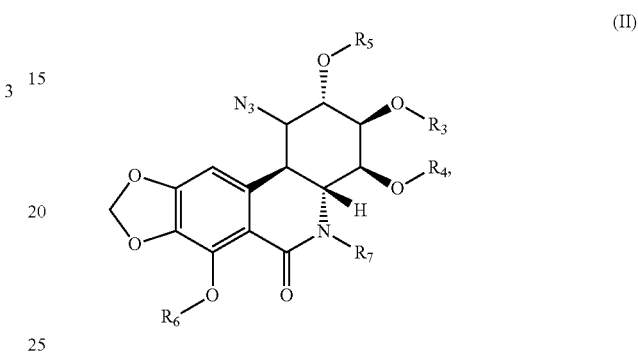

(II)

or a pharmaceutically acceptable salt thereof, an isomer or a mixture of isomers in all proportions, in particular a mixture of enantiomers, and in particular a racemate mixture, in which $R_3$, $R_4$, $R_5$, $R_6$ and $R_7$ are as defined above.

These compounds are in particular useful as synthesis intermediate, in the synthesis of the compounds of formula (I) according to the invention.

According to one particular embodiment, these compounds meet the following formula (IIbis):

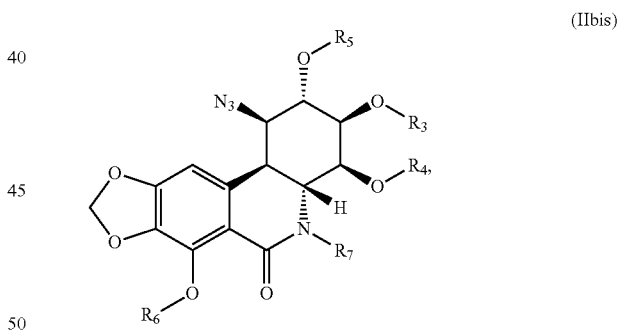

(IIbis)

for which $R_3$, $R_4$, $R_5$, $R_6$ and $R_7$ are as defined above.

Advantageously, $R_3$, $R_4$, $R_5$ and $R_6$ represent, independently of each other, a hydrogen atom or a $SO_3H$, $PO_3H_2$ or $C(O)OH$ group, preferably a hydrogen atom, or $R_3$ and $R_4$ together form a chain —$CR_8R_9$— with $R_8$ and $R_9$ as previously defined.

Equally advantageously, $R_3$, $R_5$ and $R_6$ each represent a hydrogen atom and $R_4$ represents a hydrogen atom or an $SO_3H$, $PO_3H_2$ or $C(O)OH$ group.

Preferably, all of the radicals $R_3$, $R_4$, $R_5$ et $R_6$ represent a hydrogen atom.

Advantageous, $R_7$ represents a hydrogen atom.

Preferably, the radicals $R_3$, $R_4$, $R_5$, $R_6$ and $R_7$ each represent a hydrogen atom.

In particular, it will be the compound 5 with the following formula:

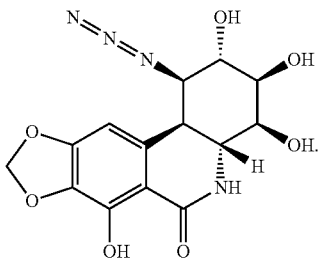

The invention will be better understood in light of the non-limiting examples which follow.

| ABBREVIATIONS: | |
|---|---|
| TLC | Thin-Layer Chromatography |
| DMSO | Dimethylsulfoxide |
| equiv. | Equivalent |
| ESI | Electrospray Ionization |
| LCMS | Liquid Chromatography-Mass Spectrometry |
| NMR | Nuclear Magnetic Resonance |
| MS | Mass spectrum |

EXAMPLE 1

Synthesis of the Compounds of the Invention

The synthesis of compound 3a below, used as a starting product, is described in *J. Org. Chem.*, 66, 2583-7, (2001).

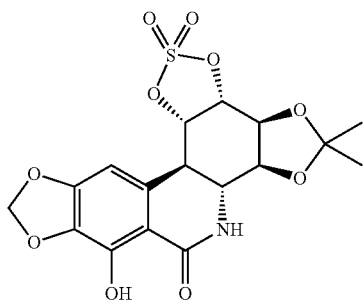

3a

Compound 5: (1R,2S,3S,4S,4aR,11bR)-1-azido-2,3, 4,7-tetrahydroxy-1,2,3,4,4a,5-hexahydro-[1,3]di-oxolo[4,5-j]phenanthridin-6(11bH)-one

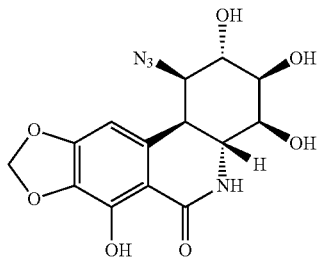 [SMILES: [N-]=[N+]=N[C@H]1[C@H](O)[C@@H](O)[C@@H](O)[C@@H]2NC(=O)c3c(cc4c(c3O)OCO4)[C@@H]12]

A mixture of sulfate 3a (224.0 mg, 0.525 mmol) and sodium azide (75.0 mg, 2.2 equiv.) in dimethylformamide (DMF) (4.0 mL) is heated at 80° C. for 7 hours. The progress of the reaction is monitored by LCMS. DMF is evaporated and the obtained residue is dissolved in tetrahydrofuran (THF) (10.0 mL) and a 20% $H_2SO_4$ aqueous solution (3.0 mL) is added. The mixture is stirred for 16 hours at ambient temperature. Silica (5.0 g) is then added to the reaction mixture, the solvents are evaporated in vacuum, and the residue is purified by silica gel chromatography (eluent: $CH_2Cl_2$/MeOH from 95/5 to 92/8) to yield the azide 5 (134.0 mg, 72% yield) in the form of a slightly yellow powder.

$^1$H NMR (400 MHz, DMSO): 13.10 (s, 1H), 7.43 (s, 1H), 6.71 (s, 1H), 6.09 (d, 1H, J=1.0 Hz), 6.07 (d, 1H, J=1.0 Hz), 5.68 (bs, 1H), 5.11 (m, 2H), 4.57 (t, 1H, J=3.0 Hz), 4.13 (bs, 1H), 3.86 (bs, 1H), 3.65 (m, 2H), 3.09 (dd, 1H, J=3.0 Hz, 12.3 Hz)

MS (ESI+) m/z 351 (MH+)

Compound 6: (1R,2S,3R,4S,4aR,11bS)-1-amino-2,3, 4,7-tetrahydroxy-1,2,3,4,4a,5-hexahydro-[1,3]di-oxolo[4,5-j]phenanthridin-6(11bH)-one

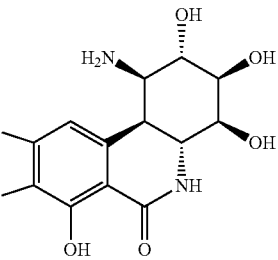

A mixture of azide 5 (30.0 mg, 0.086 mmol) and palladium (10% weight on activated carbon, 30.0 mg) in THF (2.0 mL) and ethanol (2.0 mL) is stirred at ambient temperature under hydrogen atmosphere (double rubber balloon) for 5 hours, the reaction being monitored by TLC. The crude is filtered on Celite ($CH_2Cl_2$/MeOH 9/1), and after evaporation, purified by silica gel chromatography (eluent: $CH_2Cl_2$/MeOH from 90/10 to 80/20) to yield the amine (15.0 mg, 54% yield) in the form of a white powder.

$^1$H NMR (400 MHz, DMSO): 13.10 (bs, 1H), 7.44 (s, 1H), 6.47 (s, 1H), 6.07 (d, 1H, J=1.0 Hz), 6.05 (d, 1H, J=1.0 Hz), 5.20 (bs, 1H), 4.93 (bs, 1H), 3.94 (m, 1H), 3.79 (bs, 1H), 3.71 (m, 2H), 3.59 (bs, 1H), 3.05 (m, 1H)

MS (ESI+) m/z 325 (MH+)

Compound 7: (3aS,3bS,6aS,6bR,13bR,13cS)-9-hydroxy-5,5-dimethyl-3b,6a,6b,7,13b,13c-hexahydrotris[1,3]dioxolo[4,5-a:4',5'-c:4'',5''-j]phenanthridine-2,8(3aH)-dione (synthesis intermediate)

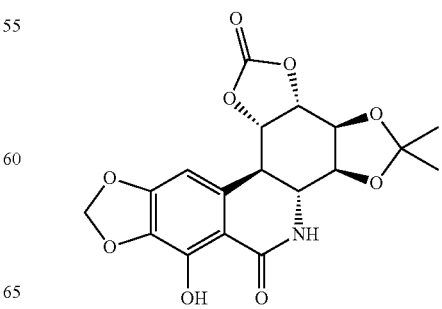

Triphosgene (32.0 mg, 2.0 equiv.), then triethylamine (10.0 µL, 1.3 equiv.) are added to a "diol" solution (20 mg, 0.054 mmol), compound no. 8 from the reference *J. Org. Chem.*, 66, 2583-7, (2001), in a mixture of tetrahydrofuran (0.5 mL) and dichloromethane (0.5 mL), the mixture is stirred for 18 hours at ambient temperature. Water is added and the mixture is extracted with dichloromethane. The organic phase is dried on magnesium sulfate, filtered and evaporated. The residue is purified on silica gel (eluent: 98/2 CH$_2$Cl$_2$/MeOH) to yield carbonate 7 (2.0 mg) in the form of an orange oil.

$^1$H NMR (400 MHz, DMSO): 13.19 (s, 1H), 8.94 (s, 1H), 6.50 (s, 1H), 6.11 (s, 1H), 6.09 (s, 1H), 5.23 (t, 1H, J=9.1 Hz), 4.87 (t, 1H, J=8.4 Hz), 4.61 (t, 1H, J=7.7 Hz), 4.48 (t, 1H, J=7.7 Hz), 3.67 (dd, 1H, J=7.7 Hz, J=14.5 Hz), 3.44 (m, 1H), 1.47 (s, 3H), 1.34 (s, 3H).

MS (ESI+) m/z 392 (MH+).

Compound 8: N-((1R,2S,3S,4S,4aR,11bR)-2,3,4,7-tetrahydroxy-6-oxo-1,2,3,4,4a,5,6,11b-octahydro-[1,3]dioxolo[4,5-j]phenanthridin-1-yl)benzenesulfonamide

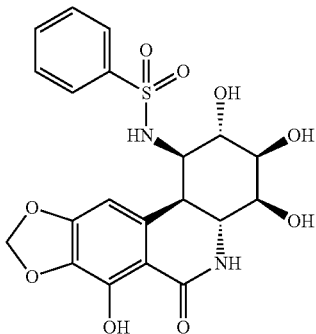 [SMILES: O=C1N[C@H]2[C@H](O)[C@H](O)[C@@H](O)[C@H](NS(=O)(=O)c3ccccc3)[C@@H]2c2cc3c(c(O)c21)OCO3]

A mixture of azide 5 (9.0 mg, 0.026 mmol) and palladium (10% weight on activated carbon, 10.0 mg) in THF (1.0 mL) and ethanol (1.0 mL) is stirred at ambient temperature under hydrogen atmosphere (double rubber balloon) for 16 hours, the reaction being monitored by TLC. Triethylamine (8.0 µL, 2.0 equiv.) followed by benzenesulfonyl chloride (5.0 µL, 1.5 equiv.) are then added at ambient temperature. After 30 minutes, the TLC indicates a complete conversion. Silica (2.0 g) is then added to the reaction mixture, the solvents are evaporated in vacuum, and the residue is purified by silica gel chromatography (eluent: CH$_2$Cl$_2$/MeOH from 98/2 to 90/10) to lead to the sulfonamide 8 (9.0 mg, 66% yield) in the form of a slightly yellow solid.

MS (ESI+) m/z 465 (MH+).

Compound 9: 1-phenyl-3-((1R,2S,3S,4S,4aR,11bR)-2,3,4,7-tetrahydroxy-6-oxo-1,2,3,4,4a,5,6,11b-octahydro-[1,3]dioxolo[4,5-j]phenanthridin-1-yl)urea

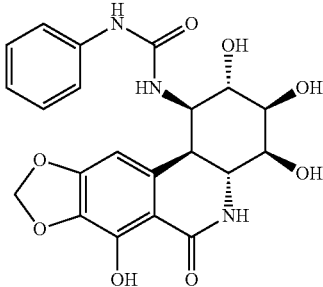 [SMILES: O=C(Nc1ccccc1)N[C@H]1[C@H](O)[C@@H](O)[C@@H](O)[C@@H]2NC(=O)c3c(cc4c(c3O)OCO4)[C@@H]12]

A mixture of azide 5 (9.0 mg, 0.026 mmol) and palladium (10% weight on activated carbon, 10.0 mg) in THF (1.0 mL) and ethanol (1.0 mL) is stirred at ambient temperature under hydrogen atmosphere (double rubber balloon) for 16 hours, the reaction being monitored by TLC. Triethylamine (5.0 µL, 2.0 equiv.) followed by phenyl isocyanate (5.0 µL, 1.5 equiv.) are then added at ambient temperature. After 2 hours, the TLC indicates a complete conversion. Silica (2.0 g) is then added to the reaction mixture, the solvents are evaporated in vacuum, and the residue is purified by silica gel chromatography (eluent: CH$_2$Cl$_2$/MeOH from 98/2 to 85/15) to lead to the phenylurea 9 in the form of a slightly yellow solid (4.6 mg, 41% yield).

MS (ESI+) m/z 444 (MH+).

Compound 10: tert-butyl (1R,2S,3S,4S,4aR,11bR)-2,3,4,7-tetrahydroxy-6-oxo-1,2,3,4,4a,5,6,11b-octahydro-[1,3]dioxolo[4,5-j]phenanthridin-1-ylcarbamate

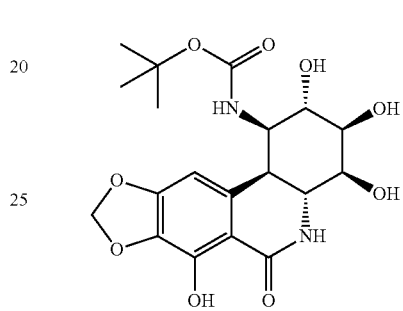

A mixture of azide 5 (9.0 mg, 0.026 mmol) and palladium (10% weight on activated carbon, 10.0 mg) in THF (1.0 mL) and ethanol (1.0 mL) is stirred at ambient temperature under hydrogen atmosphere (double rubber balloon) for 16 hours, the reaction being monitored by TLC. Triethylamine (17.0 µL, 5.0 equiv.) followed by di-tert-butyl carbonate (19.0 µL, 5.0 equiv.) are then added at ambient temperature. After 5 hours, the TLC indicates a complete conversion. Silica (2.0 g) is then added to the reaction mixture, the solvents are evaporated in vacuum, and the residue is purified by silica gel chromatography (eluent: CH$_2$Cl$_2$/MeOH from 98/2 to 90/10) to yield the tert-butylcarbamate 10 in the form of a slightly yellow solid (6.4 mg, 58% yield).

MS (ESI+) m/z 425 (MH+).

Compounds 11 and 12: (1R,2S,3S,4S,4aR,11bR)-2,3,4,7-tetrahydroxy-1-(4-phenyl-1H-1,2,3-triazol-1-yl)-1,2,3,4,4a,5-hexahydro-[1,3]dioxolo[4,5-j]phenanthridin-6(11bH)-one (11) and (1R,2S,3S,4S,4aR,11bR)-2,3,4,7-tetrahydroxy-1-(5-phenyl-1H-1,2,3-triazol-1-yl)-1,2,3,4,4a,5-hexahydro-[1,3]dioxolo[4,5-j]phenanthridin-6(11bH)-one (12)

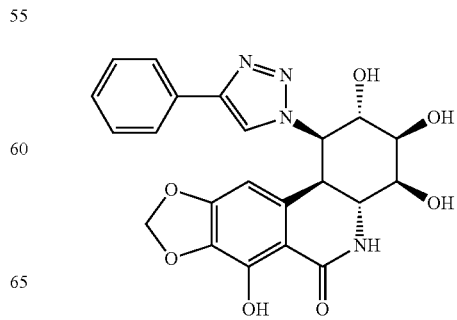

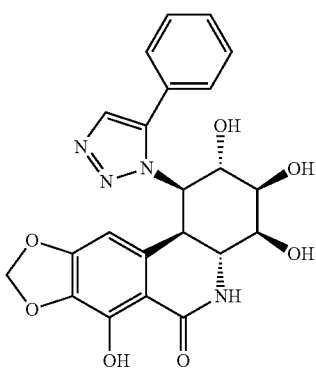

A mixture of azide 5 (20.0 mg, 0.057 mmol), phenylacetylene (0.6 mL) and methanol (2 drops) is heated at 100° C. for 7 hours. Silica (2.0 g) is then added to the reaction mixture, the solvents are evaporated in vacuum, and the residue is purified by silica gel chromatography (eluent: $CH_2Cl_2$/MeOH from 98/2 to 90/10) to lead to a mixture of starting product and of the two expected isomer triazoles 11 and 12. This mixture is purified by HPLC (Xterra 10×150, 5 μm; $H_2O/CH_3CN$ from 75/25 to 65/45) for 10 minutes at 5 mL/min, to yield the two triazoles.

$^1$H NMR (400 MHz, DMSO) isomer 11 (major): 13.22 (bs, 1H), 8.52 (s, 1H), 7.82 (d, 2H, J=7.5 Hz), 7.67 (s, 1H), 7.39 (t, 2H, J=7.5 Hz), 7.28 (t, 1H, J=7.5 Hz), 6.04 (s, 1H), 5.96 (s, 1H), 5.92 (s, 1H), 5.46 (m, 1H), 5.26 (bs, 1H), 4.86 (bs, 1H), 4.59 (dd, 1H, J=9.7 Hz, 13.7 Hz), 4.24 (m, 1H), 3.88 (m, 2H), 3.70 (dd, 1H, J=4.8 Hz, 13.7 Hz).

MS (ESI+) m/z 453 (MH+).

$^1$H NMR (400 MHz, DMSO) isomer 12 (minor): 13.24 (bs, 1H), 7.77 (s, 1H), 7.61 (m, 6H), 5.98 (m, 2H), 5.81 (s, 1H), 5.19 (s, 1H), 4.86 (dd, 1H, J=9.7 Hz, 13.0 Hz), 3.97 (m, 1H), 3.81 (dd, 1H, J=3.0 Hz, 9.9 Hz), 3.74 (m, 1H), 3.68 (dd, 1H, J=4.5 Hz, 13.0 Hz).

MS (ESI+) m/z 475 (MNa+).

Compound 13: 1-isobutyrilamino trans dihydronarciclasin

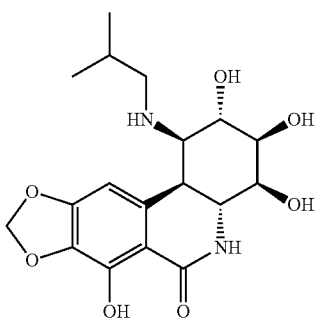 [SMILES: CC(C)CN[C@H]1[C@H](O)[C@@H](O)[C@@H](O)[C@@H]2NC(=O)c3c(cc4c(c3O)OCO4)[C@@H]12]

A mixture of amine 6 (10.0 mg, 0.031 mmol), isobutyraldehyde (10.0 μL, 3.5 equiv.) and sodium cyanoborohydride (11.0 mg, 6.0 equiv.) in THF (2.0 mL) containing molecular sieve 4 Å is stirred at ambient temperature for 16 hours. The mixture is poured into an aqueous solution of $Na_2CO_3$ and the organic phase extracted with ethyl acetate, dried on magnesium sulfate, filtered and evaporated. The residue is purified by silica gel chromatography (eluent: $CH_2Cl_2$/MeOH/$NH_4OH$ 9/1/0.1) to yield the amine 13 (4.6 mg, 39% yield) in the form of a white powder.

$^1$H NMR (400 MHz, DMSO): 13.18 (s, 1H), 7.46 (s, 1H), 6.35 (s, 1H), 6.07 (s, 1H), 6.5 (s, 1H), 5.76 (bs, 1H), 5.24 (d, 1H, J=3.8 Hz), 4.91 (d, 1H, J=6.6 Hz), 4.10 (m, 1H), 3.79 (bs, 1H), 3.69 (m, 2H), 3.22 (bs, 1H), 3.15 (m, 1H), 2.58 (m, 1H), 2.44 (m, 1H), 1.57 (h, 1H, J=6.6 Hz), 0.82 (dd, 6H, J=1.6 Hz, 6.6 Hz).

MS (ESI+) m/z 381 (MH+).

Compound 14: (1R,2S,3R,4S,4aR,11bS)-1-(benzylamino)-2,3,4,7-tetrahydroxy-1,2,3,4,4a,5-hexahydro-[1,3]dioxolo[4,5-j]phenanthridin-6(11bH)-one

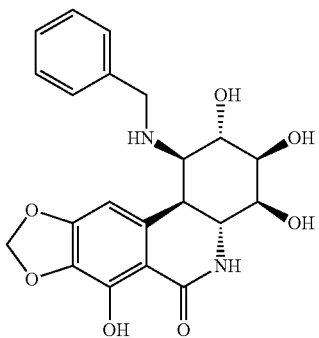 [SMILES: O=C1N[C@H]2[C@H](O)[C@H](O)[C@@H](O)[C@H](NCc3ccccc3)[C@@H]2c2cc3c(c(O)c21)OCO3]

A mixture of amine 6 (57.0 mg, 0.176 mmol), benzaldehyde (35.0 μL, 2.0 equiv.) and sodium cyanoborohydride (34.0 mg, 3.0 equiv.) in THF (10.0 mL) containing molecular sieve 4 Å is stirred at ambient temperature for 48 hours. The mixture is poured into an aqueous solution of $Na_2CO_3$ and the organic phase extracted with ethyl acetate, dried on magnesium sulfate, filtered and evaporated. The residue is purified by silica gel chromatography (eluent: $CH_2Cl_2$/MeOH/$NH_4OH$ 9/1/0.1) to yield the amine 14 (37.0 mg, 50% yield) in the form of a white powder.

$^1$H NMR (400 MHz, DMSO): 13.17 (s, 1H), 7.45 (s, 1H), 7.30 (m, 5H), 6.07 (s, 2H), 6.06 (s, 1H), 6.03 (s, 1H), 5.71 (bs, 1H), 5.26 (bs, 1H, J=3.8 Hz), 4.95 (bs, 1H), 4.24 (m, 1H), 3.92 (m, 1H), 3.84 (m, 1H), 3.70 (m, 3H), 3.31 (m, 1H), 3.13 (m, 1H).

MS (ESI+) m/z 415 (MH+).

Compound 15: (1R,2S,3S,4S,4aR,11bR)-2,3,4,7-tetrahydroxy-1-(piperidin-1-yl)-1,2,3,4,4a,5-hexahydro-[1,3]dioxolo[4,5-j]phenanthridin-6(11bH)-one

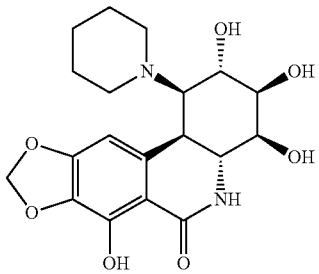 [SMILES: O=C1N[C@H]2[C@H](O)[C@H](O)[C@@H](O)[C@H](N3CCCCC3)[C@@H]2c2cc3c(c(O)c21)OCO3]

A mixture of amine 6 (30.0 mg, 0.09 mmol), glutaraldehyde (185.0 μL, 25% aqueous, 5.0 equiv.) and sodium cyanoborohydride (58.0 mg, 10.0 equiv.) in methanol (5.0 mL) is stirred at ambient temperature for 1 hour. The mixture is poured into an aqueous solution of Na₂CO₃ and the organic phase extracted with ethyl acetate, dried on magnesium sulfate, filtered and evaporated. The residue is purified by silica gel chromatography (eluent: CH₂Cl₂/MeOH/NH₄OH 9/1/0.1) to yield the amine 15 (17.0 mg, 48% yield) in the form of a white powder.

¹H NMR (400 MHz, DMSO): 13.46 (s, 1H), 7.37 (s, 1H), 6.63 (s, 1H), 6.13 (bs, 1H), 6.09 (s, 1H), 6.06 (s, 1H), 5.45 (bs, 1H), 4.88 (bs, 1H, J=3.8 Hz), 4.28 (m, 1H), 3.80 (m, 1H), 3.72 (m, 1H), 3.64 (m, 1H), 3.53 (m, 1H), 3.37 (m, 1H), 2.57 (m, 4H), 1.41 (m, 6H).

MS (ESI+) m/z 393 (MH+).

Compound 16: (1R,2S,3S,4S,4aR,11bR)-1-(dimethylamino)-2,3,4,7-tetrahydroxy-1,2,3,4,4a,5-hexahydro-[1,3]dioxolo[4,5-j]phenanthridin-6(11bH)-one

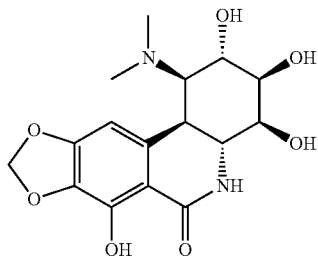 [SMILES: CN(C)[C@H]1[C@H](O)[C@@H](O)[C@@H](O)[C@@H]2NC(=O)c3c(cc4c(c3O)OCO4)[C@H]21]

A mixture of amine 6 (5.0 mg, 0.0154 mmol), formaldehyde (10.0 µL, 25% aqueous, 8.0 equiv.) and sodium cyanoborohydride (9.0 mg, 10.0 equiv.) in the methanol (0.5 mL) and acetic acid (50.0 µL) is stirred at ambient temperature for 5 hours. The mixture is poured into an aqueous solution of Na₂CO₃ and the organic phase extracted with ethyl acetate, dried on magnesium sulfate, filtered and evaporated. The residue is purified by silica gel chromatography (eluent: CH₂Cl₂/MeOH/NH₄OH 9/1/0.5) to yield the amine 16 (3.0 mg) in the form of a white powder.

¹H NMR (400 MHz, DMSO): 13.43 (s, 1H), 7.86 (s, 1H), 6.67 (s, 1H), 6.06 (s, 2H), 5.89 (m, 1H), 5.45 (m, 1H), 4.86 (m, 1H), 4.30 (m, 1H), 3.85 (m, 1H), 3.72 (m, 1H), 3.64 (m, 1H), 3.53 (m, 1H), 2.26 (s, 6H).

MS (ESI+) m/z 353 (MH+).

Compound 17: (1R,2S,3R,4S,4aR,11bS)-1-(cyclohexylamino)-2,3,4,7-tetrahydroxy-1,2,3,4,4a,5-hexahydro-[1,3]dioxolo[4,5-j]phenanthridin-6(11bH)-one

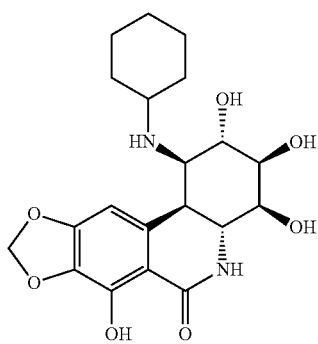 [SMILES: O=C1N[C@H]2[C@H](O)[C@H](O)[C@@H](O)[C@H](NC3CCCCC3)[C@@H]2c2cc3c(c(O)c21)OCO3]

A mixture of amine 6 (20.0 mg, 0.0617 mmol), cyclohexanone (31.0 µL, 5.0 equiv.) and sodium cyanoborohydride (38.8 mg, 10.0 equiv.) in methanol (0.5 mL) is stirred at ambient temperature for 18 hours. The mixture is poured into an aqueous solution of Na₂CO₃ and the organic phase extracted with ethyl acetate, dried on magnesium sulfate, filtered and evaporated. The residue is purified by silica gel chromatography (eluent: CH₂Cl₂/MeOH/NH₄OH 95/5/0.5) to yield the amine 17 (13.0 mg) in the form of a slightly yellow powder.

¹H NMR (400 MHz, DMSO): 13.22 (s, 1H), 7.42 (s, 1H), 6.40 (s, 1H), 6.07 (s, 1H), 6.05 (s, 1H), 5.80 (m, 1H), 5.21 (m, 1H), 4.94 (m, 1H), 4.11 (m, 1H), 3.78 (m, 1H), 3.67 (m, 2H), 3.45 (m, 1H), 3.17 (m, 1H), 2.10 (m, 1H), 1.85 (m, 1H), 1.67 (m, 3H), 1.55 (m, 1H), 1.21 (m, 2H), 1.06 (m, 2H), 0.87 (m, 1H).

MS (ESI+) m/z 407 (MH+).

Compound 18: N-((1R,2S,3R,4S,4aR,11bS)-2,3,4,7-tetrahydroxy-6-oxo-1,2,3,4,4a,5,6,11b-octahydro-[1,3]dioxolo[4,5-j]phenanthridin-1-yl)acetamide

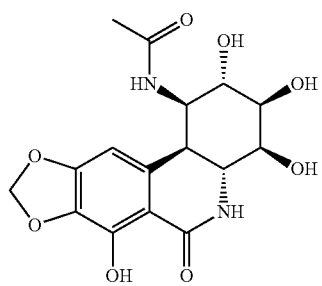 [SMILES: CC(=O)N[C@H]1[C@H](O)[C@@H](O)[C@@H](O)[C@@H]2NC(=O)c3c(cc4c(c3O)OCO4)[C@@H]12]

Triethylamine (42.0 µL, 5.0 equiv.) followed by acetic anhydride (12.0 µL, 2.0 equiv.) are added to a solution of amine 6 (20.0 mg, 0.06 mmol) in a mixture of tetrahydrofuran (1.0 mL) and ethanol (1.0 mL) at ambient temperature. After 30 minutes, the TLC indicates a complete conversion. Silica (2.0 g) is then added to the reaction mixture, the solvents are evaporated in vacuum, and the residue is purified by silica gel chromatography (eluent: CH₂Cl₂/MeOH from 98/2 to 90/10) to lead to the amide 18 in the form of a slightly yellow powder (8.0 mg, 29% yield).

MS (ESI+) m/z 367 (MH+).

Compound 19: 2-phenyl-N-((1R,2S,3R,4S,4aR,11bS)-2,3,4,7-tetrahydroxy-6-oxo-1,2,3,4,4a,5,6,11b-octahydro-[1,3]dioxolo[4,5-j]phenanthridin-1-yl)acetamide

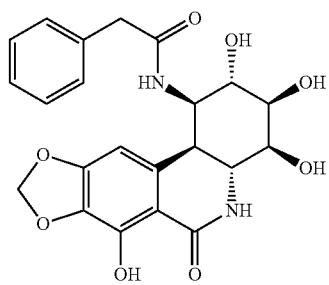 [SMILES: O=C(Cc1ccccc1)N[C@H]1[C@H](O)[C@@H](O)[C@@H](O)[C@@H]2NC(=O)c3c(cc4c(c3O)OCO4)[C@@H]12]

Triethylamine (42.0 µL, 5.0 equiv.) followed by phenylacetyl chloride (16.0 µL, 2.0 equiv.) are added to a solution of amine 6 in a mixture of tetrahydrofuran (1.0 mL) and ethanol (1.0 mL) at ambient temperature. After 30 minutes, the TLC indicates a complete conversion. Silica (2.0 g) is then added to the reaction mixture, the solvents are evaporated in vacuum, and the residue is purified by silica gel chromatography (eluent: CH$_2$Cl$_2$/MeOH from 98/2 to 90/10) to lead to the amide 19 in the form of a slightly yellow powder (13.0 mg, 47% yield).

MS (ESI+) m/z 443 (MH+).

Compound 20: N-((1R,2S,3S,4S,4aR,11bR)-2,3,4,7-tetrahydroxy-6-oxo-1,2,3,4,4a,5,6,11b-octahydro-[1,3]dioxolo[4,5-j]phenanthridin-1-yl)thiophene-2-carboxamide

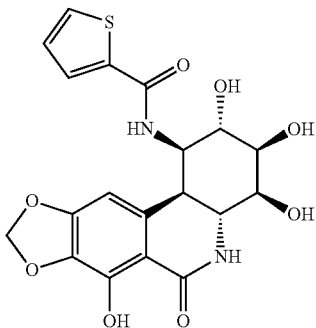 [SMILES: O=C(N[C@H]1[C@H](O)[C@@H](O)[C@@H](O)[C@@H]2NC(=O)c3c(cc4c(c3O)OCO4)[C@@H]12)c1cccs1]

Triethylamine (42.0 µL, 5.0 equiv.) followed by 2-thiophenecarboxylic acid chloride (13 µL, 2.0 equiv.) are added to a solution of amine 6 (20.0 mg, 0.06 mmol) in a mixture of tetrahydrofuran (1.0 mL) and ethanol (1.0 mL) at ambient temperature. After 30 minutes, the TLC indicates a complete conversion. Silica (2.0 g) is then added to the reaction mixture, the solvents are evaporated in vacuum, and the residue is purified by silica gel chromatography (eluent: CH$_2$Cl$_2$/MeOH from 98/2 to 90/10) to lead to the amide 20 in the form of a slightly yellow powder (14.0 mg, 52% yield).

MS (ESI+) m/z 435 (MH+).

Compound 21: N-((1R,2S,3R,4S,4aR,11bS)-2,3,4,7-tetrahydroxy-6-oxo-1,2,3,4,4a,5,6,11b-octahydro-[1,3]dioxolo[4,5-j]phenanthridin-1-yl)cyclohexanecarboxamide

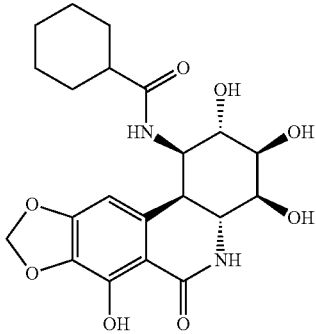 [SMILES: O=C1N[C@H]2[C@H](O)[C@H](O)[C@@H](O)[C@H](NC(=O)C3CCCCC3)[C@@H]2c2cc3c(c(O)c21)OCO3]

A mixture of azide 5 (20.0 mg, 0.057 mmol) and palladium (10% weight on activated carbon, 20.0 mg) in THF (2.0 mL) and ethanol (2.0 mL) is stirred at ambient temperature under hydrogen atmosphere (double rubber balloon) for 16 hours, the reaction being monitored by TLC. Triethylamine (17.0 µL, 2.0 equiv.) followed by cyclohexanoic acid chloride (11.5 µL, 1.5 equiv.) are then added at ambient temperature. After 5 hours, the TLC indicates a complete conversion. Silica (2.0 g) is then added to the reaction mixture, the solvents are evaporated in vacuum, and the residue is purified by silica gel chromatography (eluent: CH$_2$Cl$_2$/MeOH from 98/2 to 90/10) to yield the cyclohexyl amide 21 in the form of a slightly yellow solid (12.0 mg, 48% yield).

$^1$H NMR (400 MHz, DMSO): 13.13 (s, 1H), 7.54 (s, 1H), 7.21 (m, 1H), 6.37 (s, 1H), 6.02 (s, 1H), 6.00 (s, 1H), 5.46 (bs, 1H), 5.36 (bs, 1H), 5.24 (bs, 1H), 4.60 (m, 1H), 3.88-3.60 (m, 4H), 3.19 (m, 1H), 2.03 (m, 1H), 1.59 (m, 5H), 1.19 (m, 5H).

MS (ESI+) m/z 435 (MH+).

Compound 22: N-((1R,2S,3R,4S,4aR,11bS)-2,3,4,7-tetrahydroxy-6-oxo-1,2,3,4,4a,5,6,11b-octahydro-[1,3]dioxolo[4,5-j]phenanthridin-1-yl)benzamide

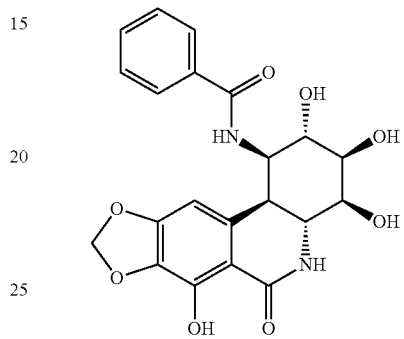

A mixture of azide 5 (36.0 mg, 0.10 mmol) and palladium (10% weight on activated carbon, 10.0 mg) in THF (1.0 mL) and ethanol (1.0 mL) is stirred at ambient temperature under hydrogen atmosphere (double rubber balloon) for 16 hours, the reaction being monitored by TLC. Triethylamine (30.0 µL, 2.0 equiv.) followed by benzoyl chloride (14.0 µL, 1.5 equiv.) are then added at ambient temperature. After 30 minutes, the TLC indicates a complete conversion. Silica (3.0 g) is then added to the reaction mixture, the solvents are evaporated in vacuum, and the residue is purified by silica gel chromatography (eluent: CH$_2$Cl$_2$/MeOH from 98/2 to 90/10) to lead to the benzamide 22 in the form of a slightly yellow powder (24.0 mg, 54% yield).

$^1$H NMR (400 MHz, DMSO): 13.16 (s, 1H), 7.95 (d, 1H, J=9.9 Hz), 7.71 (m, 2H), 7.60 (s, 1H), 7.53 (t, 1H, J=7.5 Hz), 7.45 (t, 2H, J=7.5 Hz), 6.62 (s, 1H), 6.02 (s, 1H), 5.98 (s, 1H), 5.71 (d, 1H, J=2.7 Hz), 5.65 (d, 1H, J=3.5 Hz), 5.28 (d, 1H, J=5.7 Hz), 4.87 (d, 1H, J=9.9 Hz), 4.01 (dd, 1H, J=9.9 Hz, 13.7 Hz), 3.93 (bs, 1H), 3.86 (m, 2H).

MS (ESI+) m/z 429 (MH+).

Compound 23: 4-fluoro-N-((1R,2S,3R,4S,4aR,11bS)-2,3,4,7-tetrahydroxy-6-oxo-1,2,3,4,4a,5,6,11b-octahydro-[1,3]dioxolo[4,5-j]phenanthridin-1-yl)benzamide

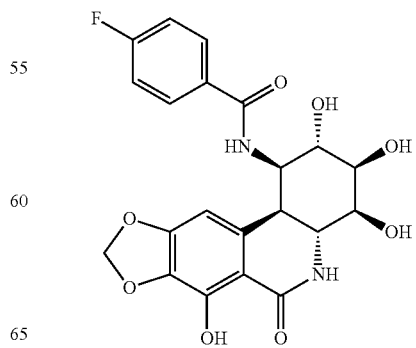

Triethylamine (42.0 mL, 5.0 equiv.) followed by 4-fluorobenzoyl chloride (14 mL, 2.0 equiv.) are added to a solution of amine 6 (20.0 mg, 0.06 mmol) in a mixture of tetrahydrofuran (1.0 mL) and ethanol (1.0 mL) at ambient temperature. After 30 minutes, the TLC indicates a complete conversion. Silica (2.0 g) is then added to the reaction mixture, the solvents are evaporated in vacuum, and the residue is purified by silica gel chromatography (eluent: CH$_2$Cl$_2$/MeOH from 98/2 to 90/10) to lead to the amide 23 in the form of a slightly yellow powder (14.0 mg, 50% yield).

MS (ESI+) m/z 447 (MH+).

Compound 24: N-((1R,2S,3R,4S,4aR,11bS)-2,3,4,7-tetrahydroxy-6-oxo-1,2,3,4,4a,5,6,11b-octahydro-[1,3]dioxolo[4,5-j]phenanthridin-1-yl)-3-(trifluoromethyl)benzamide

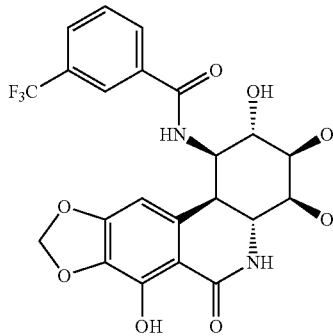 [SMILES: O=C(N[C@H]1[C@H](O)[C@@H](O)[C@@H](O)[C@@H]2NC(=O)c3c(cc4c(c3O)OCO4)[C@@H]12)c1cccc(C(F)(F)F)c1]

Triethylamine (64.0 mL, 5.0 equiv.) followed by 3-trifluoromethyl-benzoyl chloride (10.0 mL, 1.5 equiv.) are added to a solution of amine 6 (20.0 mg, 0.09 mmol) in a mixture of tetrahydrofuran (1.0 mL) and ethanol (1.0 mL) at ambient temperature. After 30 minutes, the TLC indicates a complete conversion. Silica (2.0 g) is then added to the reaction mixture, the solvents are evaporated in vacuum, and the residue is purified by silica gel chromatography (eluent: CH$_2$Cl$_2$/MeOH from 95/5 to 80/20) to lead to the amide 24 in the form of a slightly yellow powder (13.0 mg).

$^1$H NMR (400 MHz, DMSO): 13.17 (s, 1H), 8.15 (m, 2H), 8.01 (m, 2H), 7.91 (d, 1H, J=8.5 Hz), 7.71 (dd, 1H, J=8.5 Hz, J=7.5 Hz), 7.59 (s, 1H), 6.51 (s, 1H), 6.01 (s, 1H), 5.98 (s, 1H), 5.64 (bs, 1H), 5.57 (bs, 1H), 5.25 (bs, 1H), 4.87 (m, 1H), 4.15 (dd, 1H, J=9.5 Hz, J=13.2 Hz), 3.95-3.82 (m, 3H).

MS (ESI+) m/z 497 (MH+).

Compound 25: 3-cyano-N-((1R,2S,3R,4S,4aR,11bS)-2,3,4,7-tetrahydroxy-6-oxo-1,2,3,4,4a,5,6,11b-octahydro-[1,3]dioxolo[4,5-j]phenanthridin-1-yl)benzamide

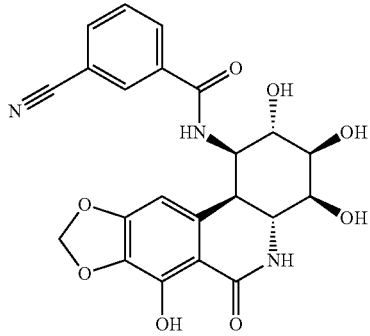 [SMILES: N#Cc1cccc(C(=O)N[C@H]2[C@H](O)[C@@H](O)[C@@H](O)[C@@H]3NC(=O)c4c(cc5c(c4O)OCO5)[C@@H]23)c1]

Triethylamine (64.0 μL, 5.0 equiv.) followed by 3-cyanobenzoyl chloride (10.0 μL, 1.5 equiv.) are added to a solution of amine 6 (20.0 mg, 0.09 mmol) in a mixture of tetrahydrofuran (1.0 mL) and ethanol (1.0 mL) at ambient temperature. After 30 minutes, the TLC indicates a complete conversion. Silica (2.0 g) is then added to the reaction mixture, the solvents are evaporated in vacuum, and the residue is purified by silica gel chromatography (eluent: CH$_2$Cl$_2$/MeOH from 95/5 to 80/20) to lead to the amide 25 in the form of a slightly yellow powder (11.0 mg).

$^1$H NMR (400 MHz, DMSO): 13.18 (s, 1H), 8.15 (m, 1H), 8.07 (m, 2H), 8.00 (d, 1H, J=7.9 Hz), 7.68 (t, 1H, J=7.9 Hz), 7.59 (s, 1H), 6.46 (s, 1H), 6.01 (s, 1H), 5.98 (s, 1H), 5.64 (m, 1H), 5.52 (m, 1H), 5.23 (m, 1H), 4.84 (m, 1H), 4.18 (dd, 1H, J=9.7 Hz, J=13.5 Hz), 3.95-3.82 (m, 3H), 2.16 (bs, 6H).

MS (ESI+) m/z 454 (MH+).

Compound 26: 3-nitro-N-((1R,2S,3R,4S,4aR,11bS)-2,3,4,7-tetrahydroxy-6-oxo-1,2,3,4,4a,5,6,11b-octahydro-[1,3]dioxolo[4,5-j]phenanthridin-1-yl)benzamide

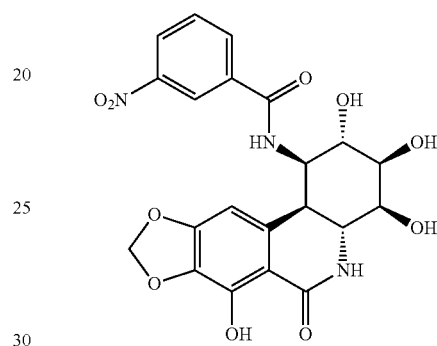

Triethylamine (64.0 μL, 5.0 equiv.) followed by 3-nitrobenzoyl chloride (10.0 μL, 1.5 equiv.) are added to a solution of amine 6 (20.0 mg, 0.09 mmol) in a mixture of tetrahydrofuran (1.0 mL) and ethanol (1.0 mL) at ambient temperature. After 30 minutes, the TLC indicates a complete conversion. Silica (2.0 g) is then added to the reaction mixture, the solvents are evaporated in vacuum, and the residue is purified by silica gel chromatography (eluent: CH$_2$Cl$_2$/MeOH from 95/5 to 80/20) to lead to the amide 26 in the form of a slightly yellow powder (10.0 mg).

$^1$H NMR (400 MHz, DMSO): 13.16 (s, 1H), 8.49 (m, 1H), 8.37 (m, 1H), 8.20 (d, 1H, J=9.8 Hz), 8.15 (m, 1H), 7.75 (t, 1H, J=7.9 Hz), 7.57 (s, 1H), 6.49 (s, 1H), 6.01 (s, 1H), 5.98 (s, 1H), 5.64 (m, 1H), 5.54 (m, 1H), 5.21 (m, 1H), 4.87 (m, 1H), 4.16 (dd, 1H, J=10.0 Hz, J=13.6 Hz), 3.95-3.80 (m, 3H), 3.34 (m, 1H).

MS (ESI+) m/z 474 (MH+).

Compound 27: 4-(chloromethyl)-N-((1R,2S,3R,4S,4aR,11bS)-2,3,4,7-tetrahydroxy-6-oxo-1,2,3,4,4a,5,6,11b-octahydro-[1,3]dioxolo[4,5-f]phenanthridin-1-yl)benzamide

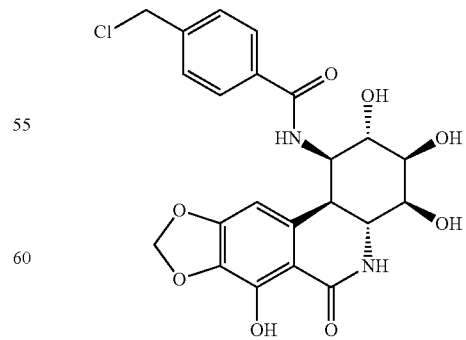

Triethylamine (98.0 μL, 5.0 equiv.) followed by 4-chloromethyl benzoyl chloride (32.0 μL, 1.2 equiv.) are added to a solution of amine 6 (46.0 mg, 0.142 mmol) in a mixture of tetrahydrofuran (3.0 mL) and ethanol (3.0 mL) at ambient temperature. After 30 minutes, the TLC indicates a complete conversion. Silica (2.0 g) is then added to the reactive mixture, the solvents are evaporated in vacuum, and the residue is purified by silica gel chromatography (eluent: $CH_2Cl_2$/MeOH from 95/5 to 80/20) to lead to the amide 27 in the form of a slightly yellow powder (50.7 mg).

$^1$H NMR (400 MHz, DMSO): 13.15 (s, 1H), 7.96 (d, 1H, J=10.0 Hz), 7.71 (d, 2H, J=8.0 Hz), 7.59 (s, 1H), 7.50 (d, 2H, J=8.0 Hz), 6.58 (s, 1H), 6.01 (s, 1H), 5.97 (s, 1H), 5.64 (m, 2H), 5.23 (m, 1H), 4.86 (m, 1H), 4.79 (s, 1H), 4.07-3.82 (m, 4H).

MS (ESI+) m/z 477 (MH+).

Compound 28: 3-((dimethylamino)methyl)-N-((1R, 2S,3R,4S,4aR,11bS)-2,3,4,7-tetrahydroxy-6-oxo-1,2, 3,4,4a,5,6,11b-octahydro-[1,3]dioxolo[4,5-j]phenanthridin-1-yl)benzamide

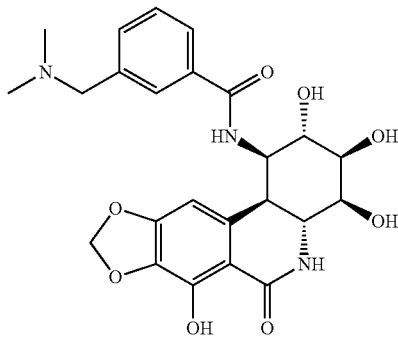 [SMILES: CN(C)Cc1cccc(C(=O)N[C@H]2[C@H](O)[C@@H](O)[C@@H](O)[C@@H]3NC(=O)c4c(cc5c(c4O)OCO5)[C@@H]23)c1]

Triethylamine (64.0 µL, 5.0 equiv.) followed by 3-chloromethyl benzoyl chloride (19.7 µL, 1.5 equiv.) are added to a solution of amine 6 (30.0 mg, 0.09 mmol) in a mixture of tetrahydrofuran (1.0 mL) and ethanol (1.0 mL) at ambient temperature. After 30 minutes, the TLC indicates a complete conversion. A dimethylamine solution (100.0 µL, 40% $H_2O$) is then added, and the mixture is heated at 60° C. for 2 hours. After returning to ambient temperature, silica (2.0 g) is then added to the reaction mixture, the solvents are evaporated in vacuum, and the residue is purified by silica gel chromatography (eluent: $CH_2Cl_2$/MeOH from 95/5 to 80/20) to lead to the amide 28 in the form of a slightly yellow powder (30.0 mg, 68% yield).

$^1$H NMR (400 MHz, DMSO): 13.17 (s, 1H), 7.96 (d, 1H, J=10.0 Hz), 7.66 (s, 1H), 7.62 (s, 1H), 7.59 (d, 1H, J=7.9 Hz), 7.46 (d, 1H, J=7.4 Hz), 7.39 (dd, 1H, J=7.9 Hz, J=7.4 Hz), 6.63 (s, 1H), 6.01 (s, 1H), 5.97 (s, 1H), 5.70 (d, 1H, J=3.7 Hz), 5.65 (d, 1H, J=3.7 Hz), 5.26 (d, 1H, J=5.9 Hz), 4.87 (m, 1H), 4.03-3.82 (m, 4H), 3.46 (bs, 2H), 2.16 (bs, 6H).

MS (ESI+) m/z 486 (MH+).

Compound 29: 4-((dimethylamino)methyl)-N-((1R, 2S,3R,4S,4aR,11bS)-2,3,4,7-tetrahydroxy-6-oxo-1,2, 3,4,4a,5,6,11b-octahydro-[1,3]dioxolo[4,5-j]phenanthridin-1-yl)benzamide

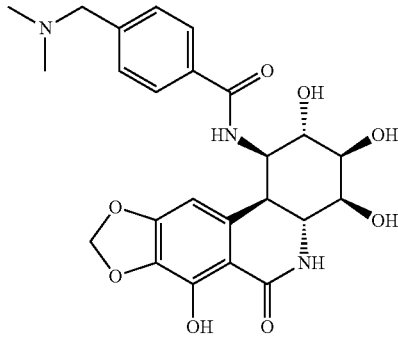 [SMILES: CN(C)Cc1ccc(C(=O)N[C@H]2[C@H](O)[C@@H](O)[C@@H](O)[C@@H]3NC(=O)c4c(cc5c(c4O)OCO5)[C@@H]23)cc1]

Triethylamine (64.0 µL, 5.0 equiv.) followed by 4-chloromethyl benzoyl chloride (2.0 equiv.) are added to a solution of amine 6 (30.0 mg, 0.09 mmol) in a mixture of tetrahydrofuran (1.0 mL) and ethanol (1.0 mL) at ambient temperature. After 30 minutes, the TLC indicates a complete conversion. A dimethylamine solution (100.0 µL, 40% $H_2O$) is then added, and the mixture is heated at 60° C. for 2 hours. After returning to ambient temperature, silica (2.0 g) is then added to the reaction mixture, the solvents are evaporated in vacuum, and the residue is purified by silica gel chromatography (eluent: $CH_2Cl_2$/MeOH from 95/5 to 80/20) to lead to the amide 29 in the form of a slightly yellow powder (27.0 mg, 61% yield).

$^1$H NMR (400 MHz, DMSO): 13.17 (s, 1H), 7.94 (d, 1H, J=10.0 Hz), 7.73-6.65 (m, 4H), 7.42 (bs, 2H), 6.61 (s, 1H), 6.01 (s, 1H), 5.97 (s, 1H), 5.70 (d, 1H, J=3.7 Hz), 5.67 (d, 1H, J=3.7 Hz), 5.33 (d, 1H, J=5.9 Hz), 4.86 (m, 1H), 4.04-3.82 (m, 4H), 2.24 (bs, 6H).

MS (ESI+) m/z 486 (MH+).

Compound 30: 3-((butylamino)methyl)-N-((1R,2S, 3R,4S,4aR,11bS)-2,3,4,7-tetrahydroxy-6-oxo-1,2,3, 4,4a,5,6,11b-octahydro-[1,3]dioxolo[4,5-j]phenanthridin-1-yl)benzamide

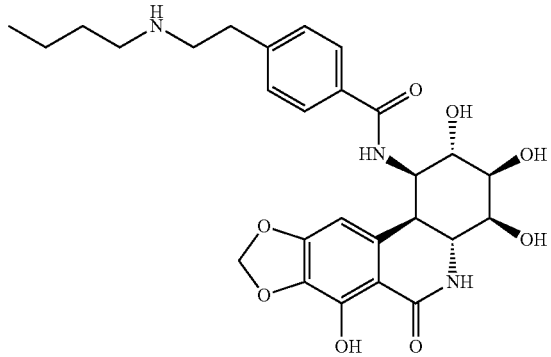 [SMILES: CCCCNCCc1ccc(C(=O)N[C@H]2[C@H](O)[C@@H](O)[C@@H](O)[C@@H]3NC(=O)c4c(cc5c(c4O)OCO5)[C@@H]23)cc1]

Triethylamine (64.0 µL, 5.0 equiv.) followed by 3-chloromethyl benzoyl chloride (19.7 µL, 1.5 equiv.) are added to a solution of amine 6 (30.0 mg, 0.09 mmol) in a mixture of tetrahydrofuran (1.0 mL) and ethanol (1.0 mL) at ambient temperature. After 30 minutes, the TLC indicates a complete conversion. Butylamine (100.0 µL) is then added, and the mixture is heated at 60° C. for 18 hours. After returning to ambient temperature, silica (2.0 g) is then added to the reaction mixture, the solvents are evaporated in vacuum, and the residue is purified by silica gel chromatography (eluent: $CH_2Cl_2$/MeOH from 95/5 to 80/20) to lead to the amide 30 in the form of a slightly yellow powder (9.0 mg).

$^1$H NMR (400 MHz, DMSO): 13.16 (s, 1H), 8.29 (s, 1H), 7.93 (d, 1H, J=9.7 Hz), 7.69 (s, 1H), 7.61 (s, 1H), 7.56 (d, 1H, J=7.3 Hz), 7.50 (d, 1H, J=7.3 Hz), 7.37 (t, 1H, J=7.3 Hz), 6.63 (s, 1H), 6.01 (s, 1H), 5.97 (s, 1H), 4.88 (m, 1H), 4.0-3.91 (m, 2H), 3.86 (m, 2H), 3.73 (s, 2H), 3.32 (m, 1H), 1.40 (m, 2H), 1.29 (m, 2H), 0.85 (t, 2H, J=7.3 Hz).

MS (ESI+) m/z 514 (MH+).

Compound 31: 3-(pyrrolidin-1-ylmethyl)-N-((1R,2S,3R,4S,4aR,11bS)-2,3,4,7-tetrahydroxy-6-oxo-1,2,3,4,4a,5,6,11b-octahydro-[1,3]dioxolo[4,5-j]phenanthridin-1-yl)benzamide

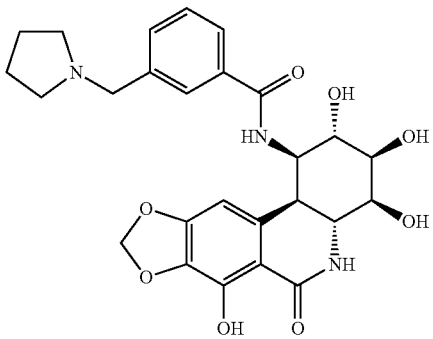 [SMILES: O=C(N[C@H]1[C@H](O)[C@@H](O)[C@@H](O)[C@@H]2NC(=O)c3c(cc4c(c3O)OCO4)[C@@H]12)c1cccc(CN2CCCC2)c1]

Triethylamine (64.0 µL, 5.0 equiv.) followed by 3-chloromethyl benzoyl chloride (19.7 µL, 1.5 equiv.) are added to a solution of amine 6 (30.0 mg, 0.09 mmol) in a mixture of tetrahydrofuran (1.0 mL) and ethanol (1.0 mL) at ambient temperature. After 30 minutes, the TLC indicates a complete conversion. Pyrrolidine (20.0 µL) is then added, and the mixture is heated at 60° C. for 2 hours. After returning to ambient temperature, silica (2.0 g) is then added to the reaction mixture, the solvents are evaporated in vacuum, and the residue is purified by silica gel chromatography (eluent: $CH_2Cl_2$/MeOH from 95/5 to 80/20) to lead to the amide 31 in the form of a slightly yellow powder (6.0 mg).

$^1$H NMR (400 MHz, DMSO): 13.16 (s, 1H), 8.24 (s, 1H), 7.94 (d, 1H, J=9.7 Hz), 7.66 (s, 1H), 7.60 (s, 1H), 7.57 (d, 1H, J=7.8 Hz), 7.47 (d, 1H, J=7.7 Hz), 7.37 (t, 1H, J=7.6 Hz), 6.63 (s, 1H), 6.01 (s, 1H), 5.97 (s, 1H), 5.71 (m, 2H), 4.88 (m, 1H), 4.0-3.82 (m, 4H), 3.56 (s, 2H), 3.32 (m, 1H), 2.41 (m, 4H), 1.69 (m, 4H).

MS (ESI+) m/z 512 (MH+).

Compound 32: 3-(morpholinomethyl)-N-((1R,2S,3R,4S,4aR,11bS)-2,3,4,7-tetrahydroxy-6-oxo-1,2,3,4,4a,5,6,11b-octahydro-[1,3]dioxolo[4,5-j]phenanthridin-1-yl)benzamide

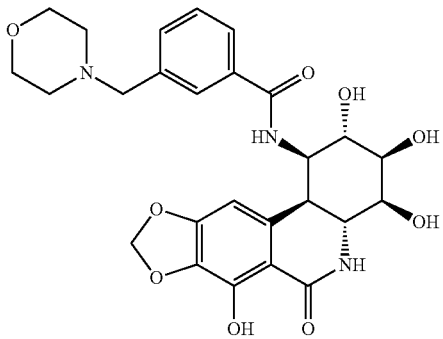 [SMILES: O=C(N[C@H]1[C@H](O)[C@@H](O)[C@@H](O)[C@@H]2NC(=O)c3c(cc4c(c3O)OCO4)[C@@H]12)c1cccc(CN2CCOCC2)c1]

Triethylamine (64.0 µL, 5.0 equiv.) followed by 3-chloromethyl benzoyl chloride (19.7 µL, 1.5 equiv.) are added to a solution of amine 6 (30.0 mg, 0.09 mmol) in a mixture of tetrahydrofuran (1.0 mL) and ethanol (1.0 mL) at ambient temperature. After 30 minutes, the TLC indicates a complete conversion. The morpholine (100.0 µL) is then added, and the mixture is heated at 60° C. for 18 hours. After returning to ambient temperature, silica (2.0 g) is then added to the reaction mixture, the solvents are evaporated in vacuum, and the residue is purified by silica gel chromatography (eluent: $CH_2Cl_2$/MeOH from 95/5 to 80/20) to lead to the amide 32 in the form of a slightly yellow powder (5.0 mg).

$^1$H NMR (400 MHz, DMSO): 13.16 (s, 1H), 8.27 (s, 1H), 7.68 (s, 1H), 7.94 (d, 1H, J=9.9 Hz), 7.66 (s, 1H), 7.60 (s, 1H), 7.57 (d, 1H, J=7.7 Hz), 7.47 (d, 1H, J=7.3 Hz), 7.39 (t, 1H, J=7.6 Hz), 6.63 (s, 1H), 6.01 (s, 1H), 5.97 (s, 1H), 5.73 (m, 2H), 4.87 (m, 1H), 4.03-3.83 (m, 4H), 3.56 (m, 4H), 3.48 (s, 2H), 3.32 (m, 1H), 2.33 (m, 4H).

MS (ESI+) m/z 528 (MH+).

Compound 33: 3-((cyclopropylamino)methyl)-N-((1R,2S,3R,4S,4aR,11bS)-2,3,4,7-tetrahydroxy-6-oxo-1,2,3,4,4a,5,6,11b-octahydro-[1,3]dioxolo[4,5-j]phenanthridin-1-yl)benzamide

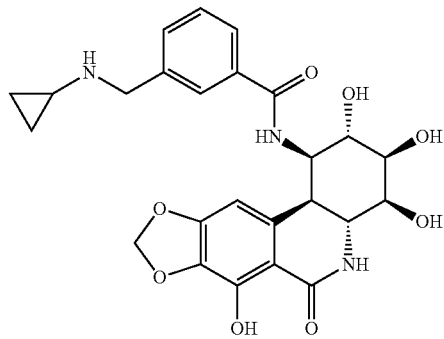 [SMILES: O=C(N[C@H]1[C@H](O)[C@@H](O)[C@@H](O)[C@@H]2NC(=O)c3c(cc4c(c3O)OCO4)[C@@H]12)c1cccc(CNC2CC2)c1]

Triethylamine (64.0 µL, 5.0 equiv.) followed by 3-chloromethyl benzoyl chloride (19.7 µL, 1.5 equiv.) are added to a solution of amine 6 (30.0 mg, 0.09 mmol) in a mixture of tetrahydrofuran (1.0 mL) and ethanol (1.0 mL) at ambient temperature. After 30 minutes, the TLC indicates a complete conversion. The cyclopropylamine (100.0 µL) is then added, and the mixture is heated at 60° C. for 18 hours. After returning to ambient temperature, silica (2.0 g) is then added to the reaction mixture, the solvents are evaporated in vacuum, and the residue is purified by silica gel chromatography (eluent: $CH_2Cl_2$/MeOH from 95/5 to 80/20) to lead to the amide 33 in the form of a slightly yellow powder (11.0 mg).

$^1$H NMR (400 MHz, DMSO): 13.16 (s, 1H), 7.92 (d, 1H, J=9.9 Hz), 7.68 (s, 1H), 7.60 (s, 1H), 7.56 (d, 1H, J=7.6 Hz), 7.48 (d, 1H, J=7.6 Hz), 7.37 (t, 1H, J=7.6 Hz), 6.63 (s, 1H), 6.01 (s, 1H), 5.97 (s, 1H), 5.69 (d, 1H, J=3.9 Hz), 5.64 (d, 1H, J=3.8 Hz), 5.25 (d, 1H, J=5.7 Hz), 4.88 (m, 1H), 4.0-3.82 (m, 4H), 3.75 (s, 2H), 2.03 (bs, 1H), 0.35 (m, 2H), 0.26 (m, 2H).

MS (ESI+) m/z 498 (MH+).

Compound 34

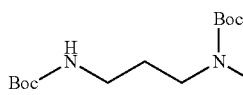

Triethylamine (50 μL, 5.0 equiv.) followed by triBoc-spermine (201.0 mg, 5.0 equiv.), the preparation of which is described in *Tetrahedron*, 56, 2449-60, (2000), are added to a solution of amide 27 (30.0 mg, 0.0798 mmol) in DMF (1.5 mL) at ambient temperature. After 5 days, the TLC indicates a complete conversion. Di-tert-butyl carbonate (170.0 μL, 10 equiv.) and triethylamine (110.0 μL, 10 equiv.) are then added and the mixture is stirred at ambient temperature for 3 hours. Silica (2.0 g) is then added to the reaction mixture, the solvents are evaporated in vacuum, and the residue is purified by silica gel chromatography (eluent: $CH_2Cl_2$/MeOH from 98/2) to lead to the amide 34 in the form of a slightly yellow powder (39.3 mg).

MS (ESI+) m/z 528 (MH+).

Compound 35: 4-((3-(4-(3-aminopropylamino)butylamino)propylamino)methyl)-N-((1R,2S,3R,4S,4aR,11bS)-2,3,4,7-tetrahydroxy-6-oxo-1,2,3,4,4a,5,6,11b-octahydro-[1,3]dioxolo[4,5-j]phenanthridin-1-yl)benzamide

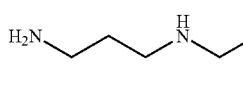

A mixture of amide 34 (37.0 mg, 0.035 mmol) and hydrochloride acid (2.0 mL, 5N in isopropanol) in isopropanol (3.0 mL) is stirred at ambient temperature for 24 hours. The residue is evaporated to dryness to lead to the amide 35 (tetrahydrochloride) in the form of a white powder (25.0 mg).

$^1$H NMR (400 MHz, DMSO): 13.18 (s, 1H), 7.98 (d, 1H, J=10.4 Hz), 7.76 (d, 2H, J=8.3 Hz), 7.66 (m, 3H), 6.60 (s, 1H), 6.01 (s, 1H), 5.98 (s, 1H), 4.86 (m, 1H), 4.18 (m, 2H), 4.02 (dd, 1H, J=9.8 Hz, J=13.4 Hz), 3.94 (m, 1H), 3.89-3.84 (m, 2H), 3.33 (m, 1H), 2.93 (m, 12H), 2.09 (m, 2H), 1.99 (m, 2H), 1.71 (m, 4H).

MS (ESI+) m/z 643 (MH+).

Compound 36: N-((1R,2S,3R,4S,4aR,11bS)-2,3,4,7-tetrahydroxy-6-oxo-1,2,3,4,4a,5,6,11b-octahydro-[1,3]dioxolo[4,5-j]phenanthridin-1-yl)-2-naphthamide

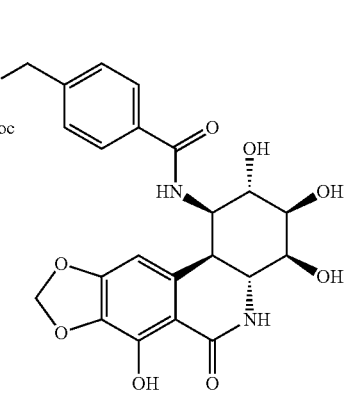

Triethylamine (64.0 μL, 5.0 equiv.) followed by naphthaloyl chloride (10.0 μL, 1.5 equiv.) are added to a solution of amine 6 (20.0 mg, 0.09 mmol) in a mixture of tetrahydrofuran (1.0 mL) and ethanol (1.0 mL) at ambient temperature. After 30 minutes, the TLC indicates a complete conversion. Silica (2.0 g) is then added to the reaction mixture, the solvents are evaporated in vacuum, and the residue is purified by silica gel chromatography (eluent: $CH_2Cl_2$/MeOH from 95/5 to 80/20) to lead to the amide 36 in the form of a slightly yellow powder (12.0 mg).

¹H NMR (400 MHz, DMSO): 13.17 (s, 1H), 8.34 (s, 1H), 8.12 (m, 1H), 7.99 (m, 3H), 7.80 (m, 1H), 7.60 (m, 3H), 6.66 (s, 1H), 6.01 (s, 1H), 5.95 (s, 1H), 5.79 (bs, 1H) 5.67 (m, 1H), 4.94 (m, 1H), 4.10 (dd, 1H, J=9.6 Hz, J=13.3 Hz), 3.99-3.84 (m, 3H).

MS (ESI+) m/z 479 (MH+).

Compound 37: 2-((dimethylamino)methyl)-N-((1R,2S,3R,4S,4aR,11bS)-2,3,4,7-tetrahydroxy-6-oxo-1,2,3,4,4a,5,6,11b-octahydro-[1,3]dioxolo[4,5-j]phenanthridin-1-yl)benzamide

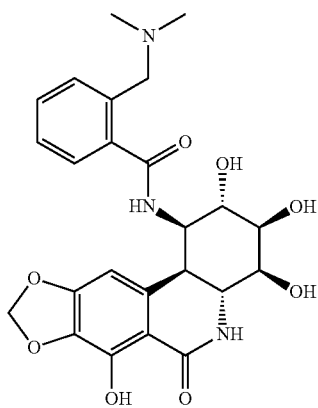 [SMILES: CN(C)Cc1ccccc1C(=O)N[C@H]1[C@H](O)[C@@H](O)[C@@H](O)[C@@H]2NC(=O)c3c(cc4c(c3O)OCO4)[C@@H]12]

Triethylamine (64.0 µL, 5.0 equiv.) followed by 2-bromomethylbenzoyl chloride (42.0 mg, 2.0 equiv.) are added to a solution of amine 6 (30.0 mg, 0.09 mmol) in a mixture of tetrahydrofuran (1.0 mL) and ethanol (1.0 mL) at ambient temperature. After 30 minutes, the TLC indicates a complete conversion. A dimethylamine solution (100.0 µL, 40% H₂O) is then added, and the mixture is heated at 60° C. for 2 hours. After return to ambient temperature, silica (2.0 g) is then added to the reactive mixture, the solvents are evaporated in vacuum, and the residue is purified by silica gel chromatography (eluent: CH₂Cl₂/MeOH from 95/5 to 80/20) to lead to the amide 37 in the form of a slightly yellow powder (19.0 mg, 43% yield).

¹H NMR (400 MHz, DMSO): 13.15 (s, 1H), 8.99 (d, 1H, J=9.6 Hz), 7.55 (m, 2H), 7.34 (m, 3H), 6.46 (s, 1H), 6.04 (s, 1H), 6.01 (s, 1H), 5.55 (d, 1H, J=3.7 Hz), 5.10 (m, 2H), 4.84 (m, 1H), 3.93-3.76 (m, 4H), 3.25 (d, 1H, J=12.4 Hz), 3.11 (d, 1H, J=12.4 Hz), 1.90 (s, 6H).

MS (ESI+) m/z 486 (MH+).

EXAMPLE 2

Cytotoxic Activity of the Compounds of the Invention

The cytotoxic activity of the compounds prepared according to the invention was evaluated by measuring inhibition of the cell proliferation of tumoral lines of human origin, such as line A549 (lung) and line HCT 116 (colon). This activity is expressed by IC₅₀, concentration of the tested product capable of inhibiting 50% of cell proliferation. The method used is luminescence measurement of the residual ATP after 72 hours of incubation using the "ATPLite®" kit marketed by Perkin Elmer, as described in the following publication: "Measurement of cytotoxicity by ATP-based luminescence assay in primary cell cultures and cell lines". I. A. Cree, P. E. Andreotti, *Toxicology in Vitro*, 11, 553-6, (1997).

As an example, the cytotoxic properties of several compounds of the invention evaluated on lines A549 and HCT 116 are reported in Table 1, in comparison with narciclasine 1 used as a reference product. The concentration values are expressed in nanomolar (nM).

TABLE 1

| Tested product | $IC_{50}$ (nM) | |
| --- | --- | --- |
|  | A549 | HCT116 |
| Narciclasine 1 | 49 | 22 |
| Compound 5 | 68 | 36 |
| Compound 6 | 60 | 35 |
| Compound 10 | 270 | 32 |
| Compound 13 | 24 | 12 |
| Compound 14 | 22 | 12 |
| Compound 16 | 150 | 81 |
| Compound 21 | 46 | 13 |
| Compound 22 | 8.7 | 4.7 |
| Compound 28 | 110 | 130 |

One thus notes that the values of $IC_{50}$ of the compounds of the invention are similar or superior to those of narciclasine.

EXAMPLE 3

Solubility of the Compounds of the Invention

Table 2 below groups together the results of solubility measurements of several compounds of the invention in comparison with narciclasine 1 used as a reference product. These results are expressed in concentration of the tested compound according to two numbers: molarity (µM) and mass by volume unit (µg/mL). The solvent used is constituted by a buffered solution at pH=7.2 "Dulbecco's Phosphate Buffered Saline" (D-PBS 1X), marketed by Gibco (reference 14190).

TABLE 2

| Tested product | Solubility Buffer D-PBS 1X (pH = 7.2) | |
| --- | --- | --- |
|  | µM | µg/mL |
| Narciclasine 1 | 401 | 131 |
| Compound 6 | 1340 | 508 |
| Hydrochloride of Compound 6 | 3870 | 1250 |
| Compound 22 | 867 | 393 |

In general, the compounds of the invention are more soluble than narciclasine 1, or much more soluble when they comprise a salifiable function and can therefore be obtained in the form of salts. Thus, under the same conditions, the compound 6 isolated in the hydrochloride form is soluble at 1250 µg/mL, thus close to a factor of 10 in relation to narciclasine.

The invention claimed is:

1. A compound of the following general formula (I):

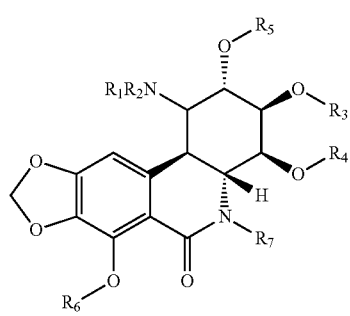
(I)

or a pharmaceutically acceptable salt thereof, an isomer or a mixture of isomers in all proportions,
in which:
- $R_1$ represents a hydrogen atom or a linear or branched $C_1$ to $C_6$ alkyl, linear or branched $C_2$ to $C_6$ alkenyl, linear or branched $C_2$ to $C_6$ alkynyl, aryl or arylalkyl group,
- $R_2$ represents a hydrogen atom, a saturated or unsaturated 3- to 7-membered hydrocarbon cycle, a 3- to 7-membered heterocycle or a linear or branched $C_1$ to $C_6$ alkyl, linear or branched $C_2$ to $C_6$ alkenyl, linear or branched $C_2$ to $C_6$ alkynyl, optionally substituted aryl, optionally substituted arylalkyl, C(O)R', SO$_2$—R', C(O)OR', C(O)NHR', NH=CNHR', C(=NR''')R', C(S)R', C(S)OR', or C(S)NHR' group, where R' and R''' represent, independently of each other, a hydrogen atom, a saturated or unsaturated 3- to 7 membered hydrocarbon cycle, an optionally substituted 3- to 7-membered heterocycle, a linear or branched $C_1$ to $C_6$ alkyl, linear or branched $C_2$ to $C_6$ alkenyl, linear or branched $C_2$ to $C_6$ alkynyl, $C_1$ to $C_6$ hydroxyalkyl, $C_1$ to $C_6$ aminoalkyl, polyamine, polyether, optionally substituted aryl, optionally substituted arylalkyl or optionally substituted heteroaryl group, or
- $R_1$ and $R_2$ form together, with the nitrogen atom bearing them, an optionally substituted heteroaryl or a 3- to 7-membered heterocycle, which can comprise 1 to 3 additional heteroatoms, and optionally substituted with a linear or branched $C_1$ to $C_6$ alkyl, linear or branched $C_2$ to $C_6$ alkenyl, linear or branched $C_2$ to $C_6$ alkynyl, aryl, arylalkyl or heteroaryl group,
- $R_3$, $R_4$, $R_5$ and $R_6$ represent, independently of each other, a hydrogen atom, a saturated or unsaturated 3- to 7-membered hydrocarbon cycle or a SO$_3$H, PO$_3$H$_2$, C(O)OH, C(O)R'', C(O)OR'', C(O)NHR'', C(S)R'', C(S)OR'', C(S)NHR'' group, where R'' represents a hydrogen atom; a saturated or unsaturated 3- to 7-membered hydrocarbon cycle; a 3- to 7-membered heterocycle optionally substituted with a linear or branched $C_1$ to $C_6$ alkyl; a linear or branched $C_1$ to $C_6$ alkyl; linear or branched $C_2$ to $C_6$ alkenyl; linear or branched $C_2$ to $C_6$ alkynyl; $C_1$ to $C_6$ hydroxyalkyl; $C_1$ to $C_6$ aminoalkyl; optionally substituted polyamine; polyether; optionally substituted aryl; or optionally substituted heteroaryl group, or $R_3$ and $R_1$ together form a —CR$_8$R$_9$—, —SO$_2$— or —PO$_2$H— chain binding the oxygen atoms bearing them,
- $R_7$ represents a hydrogen atom, a linear or branched $C_1$ to $C_6$ alkyl, linear or branched $C_2$ to $C_6$ alkenyl or linear or branched $C_2$ to $C_6$ alkynyl group or a saturated or unsaturated 3- to 7-membered hydrocarbon cycle, and
- $R_8$ and $R_9$ represent, independently of each other, a hydrogen atom or a linear or branched $C_1$ to $C_6$ alkyl group, such as a methyl.

2. The compound according to claim 1, wherein it meets the following formula (Ia):

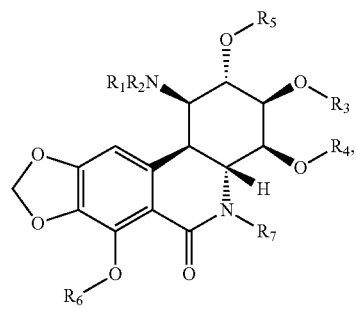
(Ia)

for which $R_1$, $R_2$, $R_3$, $R_4$, $R_5$, $R_6$ and $R_7$ are as defined in claim 1.

3. The compound according to any one of claims 1 and 2, wherein $R_3$, $R_4$, $R_5$, $R_6$ and $R_7$ each represent a hydrogen atom.

4. The compound according to any one of claims 1 and 2, wherein $R_2$ represents a group —C(O)R' with R' representing an aryl group, optionally substituted, and $R_1$ is as defined in claim 1.

5. The compound according to any one of claims 1 and 2, wherein it is chosen among the following compounds:

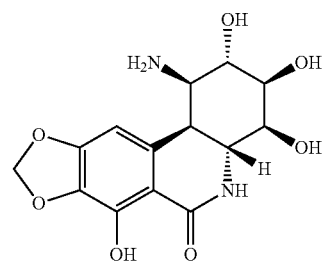
6

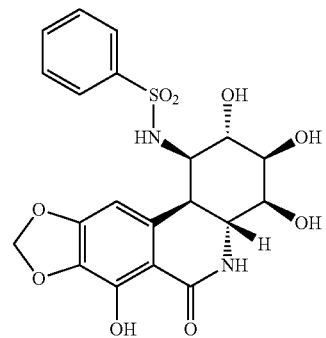
8

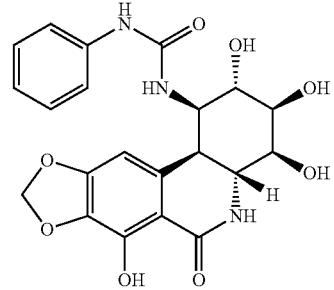
9

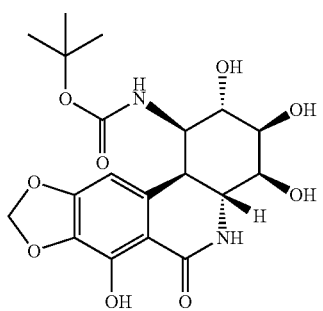
10
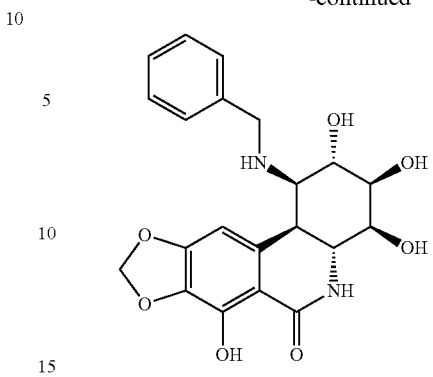
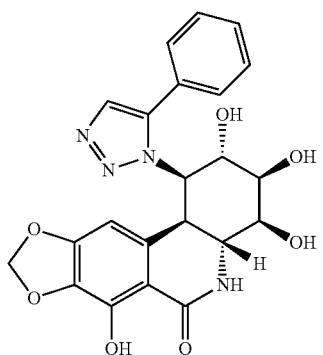
11
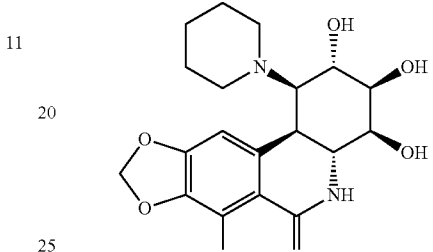
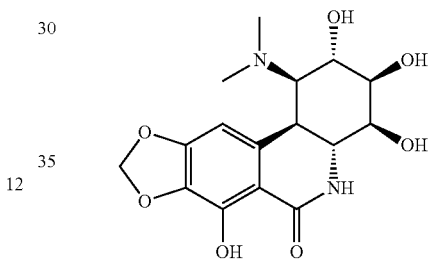
12
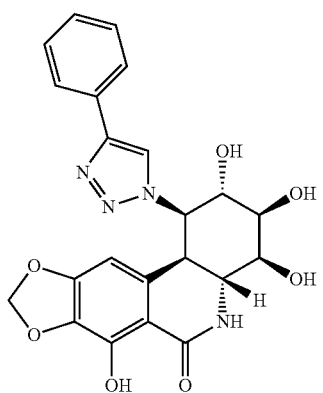
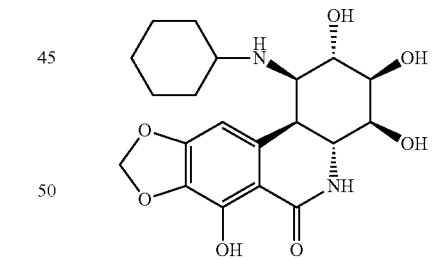
13
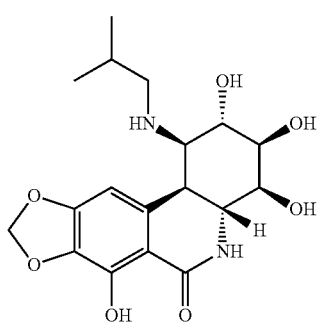
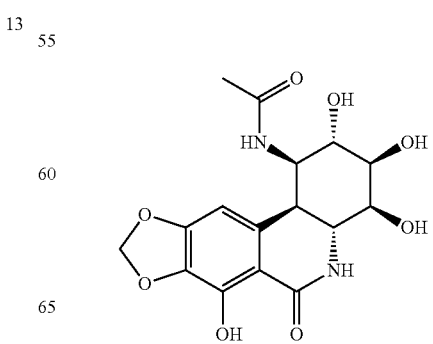

-continued
19
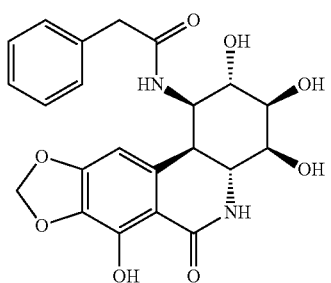
20
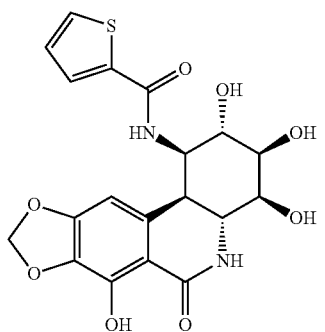
21
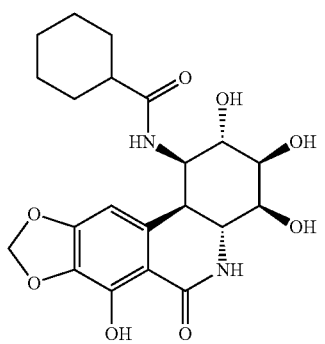
22
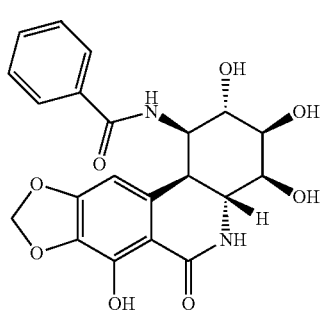
23
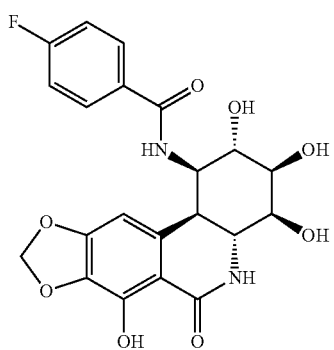
-continued
24
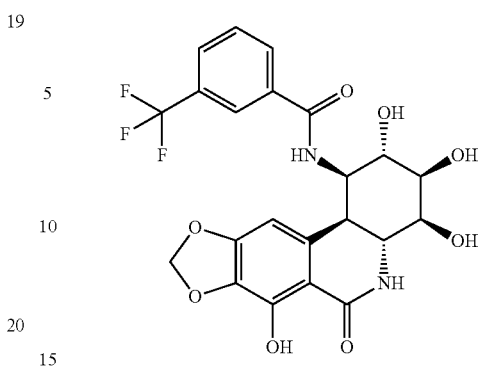
25
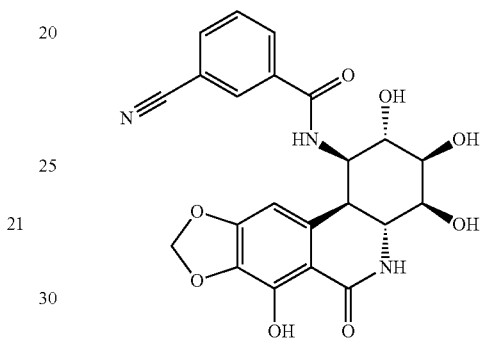
26
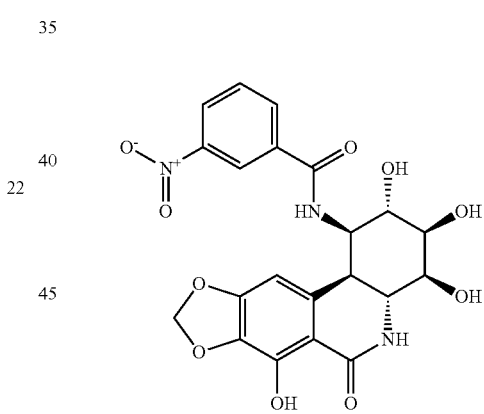
27
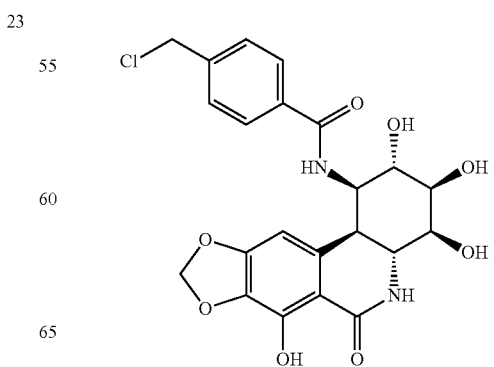

28
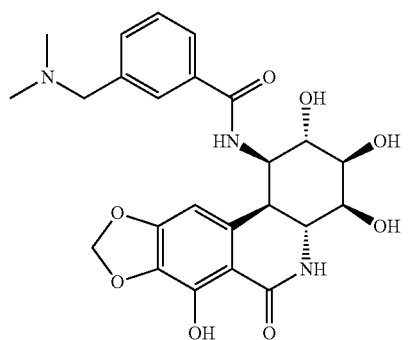
29
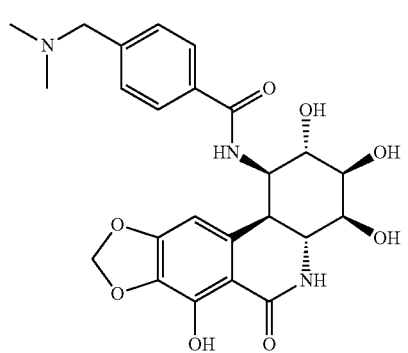
30
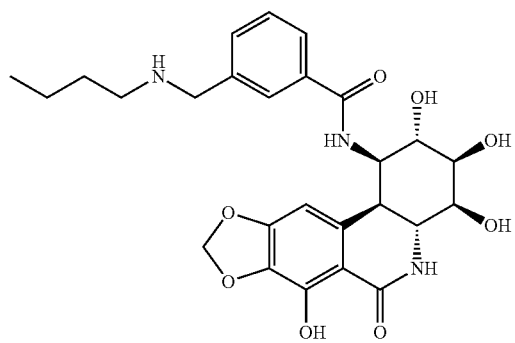
31
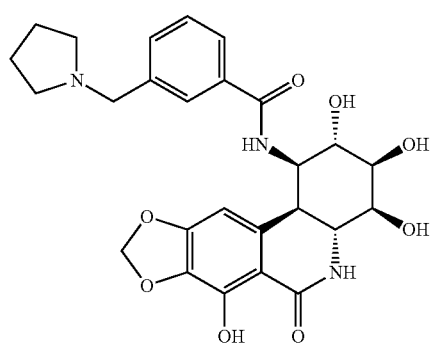
32
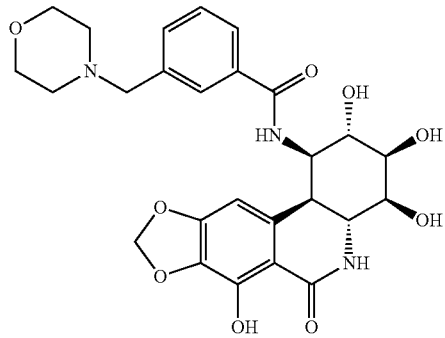
33
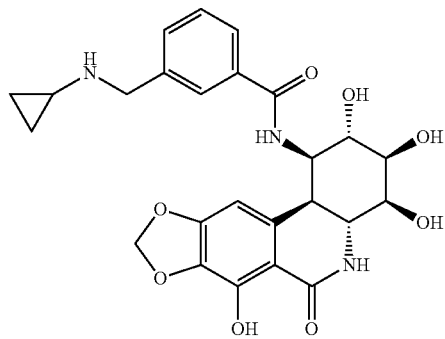
34
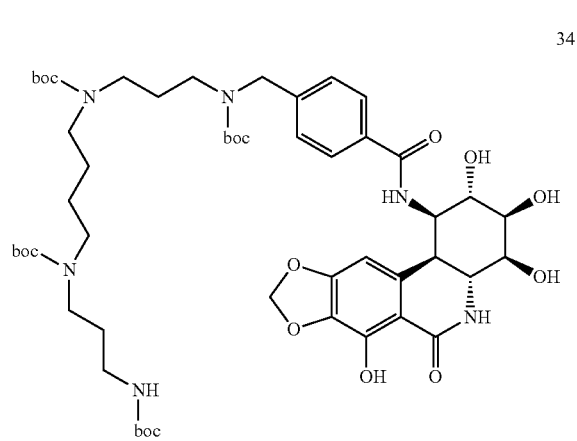
35
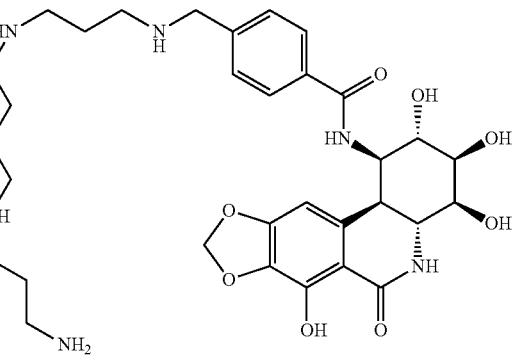

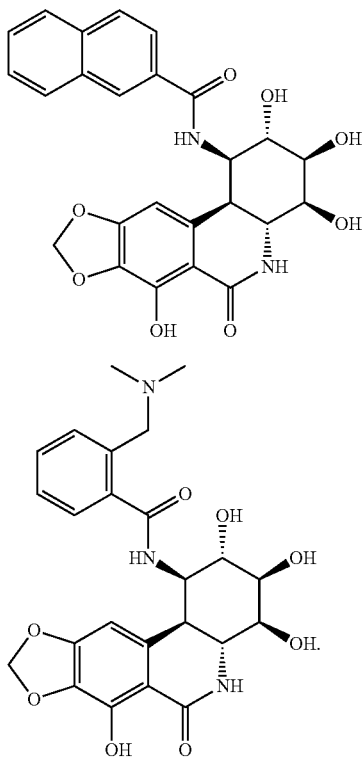

6. A pharmaceutical compound comprising at least one composition according to any one of claims 1 and 2 and at least one pharmaceutically acceptable excipient.

7. A pharmaceutical composition according to claim 6 which further comprises at least one active principle chosen from among anti-cancer agents including 6-mercaptopurine, fludarabine, cladribine, pentostatin, cytarabine, 5-fluorouracile, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocin, carboplatin, cisplatin, oxaliplatin, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrozole, letrozole, tamoxifen, octreotide or lanreotide.

8. A method for preparing a compound according to any one of claims 1 and 2, wherein the compound of formula (I) is obtained by reaction of the compound of the following formula (II):

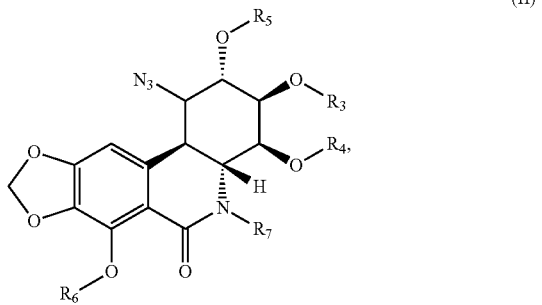

for which $R_3$, $R_4$, $R_5$, $R_6$ and $R_7$ are as defined in claim 1, and wherein the method comprises the following successive steps:

(i) hydrogenolysis of the azide of the compound of formula (II) as defined above in to free amine to yield a compound of formula (I) for which $R_1=R_2=H$, (ii) optionally one or several substitution steps of the free amine obtained in the preceding step (i) to yield a compound of formula (I) for which at least one of the $R_1$ and $R_2$ groups does not represent a hydrogen atom, and (iii) separation from the reaction medium of the compound of formula (I) obtained in the preceding step (i) or (ii).

9. The method according to claim 8, wherein in the case of a compound of formula (I), for which $R_1$ and $R_2$ together form, with the nitrogen atom bearing them, a 1,2,3-triazole optionally substituted with a linear or branched $C_1$ to $C_6$ alkyl, linear or branched $C_2$ to $C_6$ alkenyl, linear or branched $C_2$ to $C_6$ alkynyl, aryl, arylalkyl or heteroaryl group, the method comprises the following successive steps:

(i) cycloaddition of the azide of the compound of formula (II) as defined in claim 12 with an alkyne of formula A-C≡CH, for which A represents a hydrogen atom or a linear or branched $C_1$ to $C_6$ alkyl, linear or branched $C_2$ to $C_6$ alkenyl, linear or branched $C_2$ to $C_6$ alkynyl, aryl or heteroaryl group, and (ii) separation from the reaction medium of the compound of formula (I) obtained in the preceding step (i).

10. The method according to any one of claims 8 and 9, wherein the compound of formula (II) as defined in claim 8, for which the $N_3$ group is located on the same side of the cycle as the $OR_3$ group, is obtained by nucleophile substitution with a mineral azide of the compound of the following formula (III):

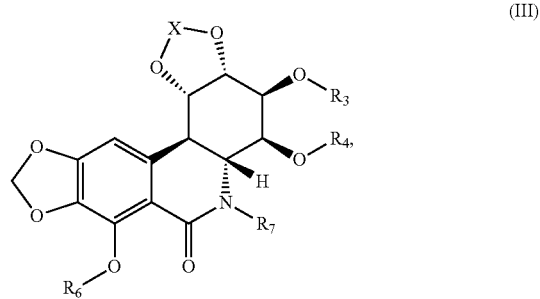

for which $R_3$, $R_4$, $R_6$ and $R_7$ are as defined in claim 1 and X represents a —SO—, —SO$_2$— or —CO— group.

11. A compound of the following formula (II):

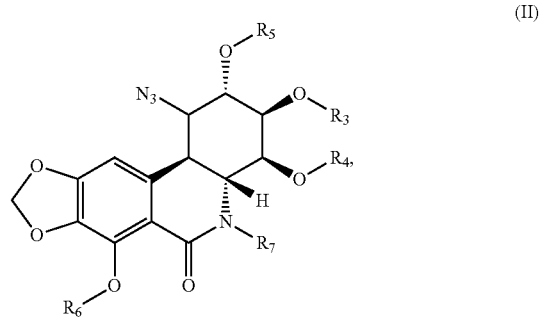

or a pharmaceutically acceptable salt thereof, an isomer or a mixture of isomers in all proportions in which $R_3$, $R_4$, $R_5$, $R_6$ and $R_7$ are as defined in claim 1.

12. The compound according to claim 11, wherein it meets the following formula:

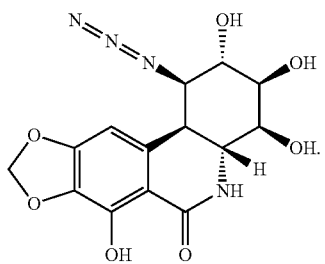

13. The compound according to claim 1, wherein the mixture of isomers is a mixture of enantiomers.

14. The compound of claim 13, wherein the mixture of enantiomers is a racemate mixture.

15. The compound according to claim 1, wherein $R_8$ and $R_9$ represent, independently of each other, a hydrogen atom or a methyl group.

16. The compound according to claim 4, wherein $R_2$ represents a group —C(O)R' with R' representing a phenyl group optionally substituted.

17. The compound according to claim 4, wherein $R_1$ represents a hydrogen atom.

18. The method according to claim 10, wherein X represents a —$SO_2$— group.

19. The compound according to claim 11, wherein the mixture of isomers is a mixture of enantiomers.

20. The compound of claim 19, wherein the mixture of enantiomers is a racemate mixture.

* * * * *